(12) United States Patent
Havel et al.

(10) Patent No.: US 10,595,982 B2
(45) Date of Patent: Mar. 24, 2020

(54) ENDOLUMINAL PROSTHESIS

(71) Applicant: Cook Medical Technologies LLC, Bloomington, IN (US)

(72) Inventors: William J. Havel, West Lafayette, IN (US); Matthew S. Huser, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 289 days.

(21) Appl. No.: 15/826,077

(22) Filed: Nov. 29, 2017

(65) Prior Publication Data

US 2018/0078359 A1 Mar. 22, 2018

Related U.S. Application Data

(62) Division of application No. 14/136,631, filed on Dec. 20, 2013, now Pat. No. 9,861,466.

(60) Provisional application No. 61/747,536, filed on Dec. 31, 2012.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/067* (2013.01); *A61F 2250/006* (2013.01)

(58) Field of Classification Search
CPC ........ A61F 2/06; A61F 2/07; A61F 2002/061; A61F 2002/065; A61F 2002/067; A61F 2250/006
See application file for complete search history.

(56) References Cited

U.S. PATENT DOCUMENTS

| | | | |
|---|---|---|---|
| 4,902,508 | A | 2/1990 | Badylak et al. |
| 5,387,235 | A | 2/1995 | Chuter |
| 5,554,389 | A | 9/1996 | Badylak et al. |
| 5,653,743 | A | 8/1997 | Martin |
| 5,824,040 | A | 10/1998 | Cox et al. |
| 5,993,844 | A | 11/1999 | Abraham et al. |
| 6,099,567 | A | 8/2000 | Badylak et al. |
| 6,206,931 | B1 | 3/2001 | Cook et al. |
| 6,224,609 | B1 | 5/2001 | Ressemann et al. |
| 7,407,509 | B2 | 8/2008 | Greenberg et al. |
| 7,846,194 | B2 | 12/2010 | Hartley et al. |
| 2001/0014823 | A1 | 8/2001 | Ressemann et al. |

(Continued)

FOREIGN PATENT DOCUMENTS

WO WO 2010/024879 A1 3/2010

OTHER PUBLICATIONS

European Search Report for corresponding EP 17206173, dated Feb. 7, 2018 (5 pages).

(Continued)

*Primary Examiner* — Ashley L Fishback
(74) *Attorney, Agent, or Firm* — Brinks Gilson & Lione

(57) ABSTRACT

An endoluminal prosthesis with a main tubular body and an auxiliary body surrounding the main tubular body to create a cavity between the main tubular body and the auxiliary body. At least one dividing wall attached to the main tubular body and the auxiliary body divides the cavity into at least two chambers, one of which has an outlet opening to the exterior of the prosthesis. Each chamber is in fluid communication with the main tubular body through fenestrations in the main tubular body and with each other.

20 Claims, 9 Drawing Sheets

(56) References Cited

U.S. PATENT DOCUMENTS

| | | |
|---|---|---|
| 2007/0250154 A1 | 10/2007 | Greenberg et al. |
| 2009/0043377 A1 | 2/2009 | Greenberg et al. |
| 2009/0125100 A1 | 5/2009 | Mead |
| 2009/0171451 A1 | 7/2009 | Kuppurathanam et al. |
| 2010/0100168 A1 | 4/2010 | Chuter et al. |
| 2013/0018297 A1 | 1/2013 | Khoury |
| 2013/0046371 A1 | 2/2013 | Greenberg et al. |

OTHER PUBLICATIONS

Examination Report for corresponding EP 13199491 dated Aug. 3, 2016 (6 pages).
European Search Report for Eureopean Patent Application No. 13199491 dated Sep. 18, 2014 (4 pages).
Partial European Search Report for European Patent Application No. 13199491 dated Apr. 15, 2014 (3 pages).

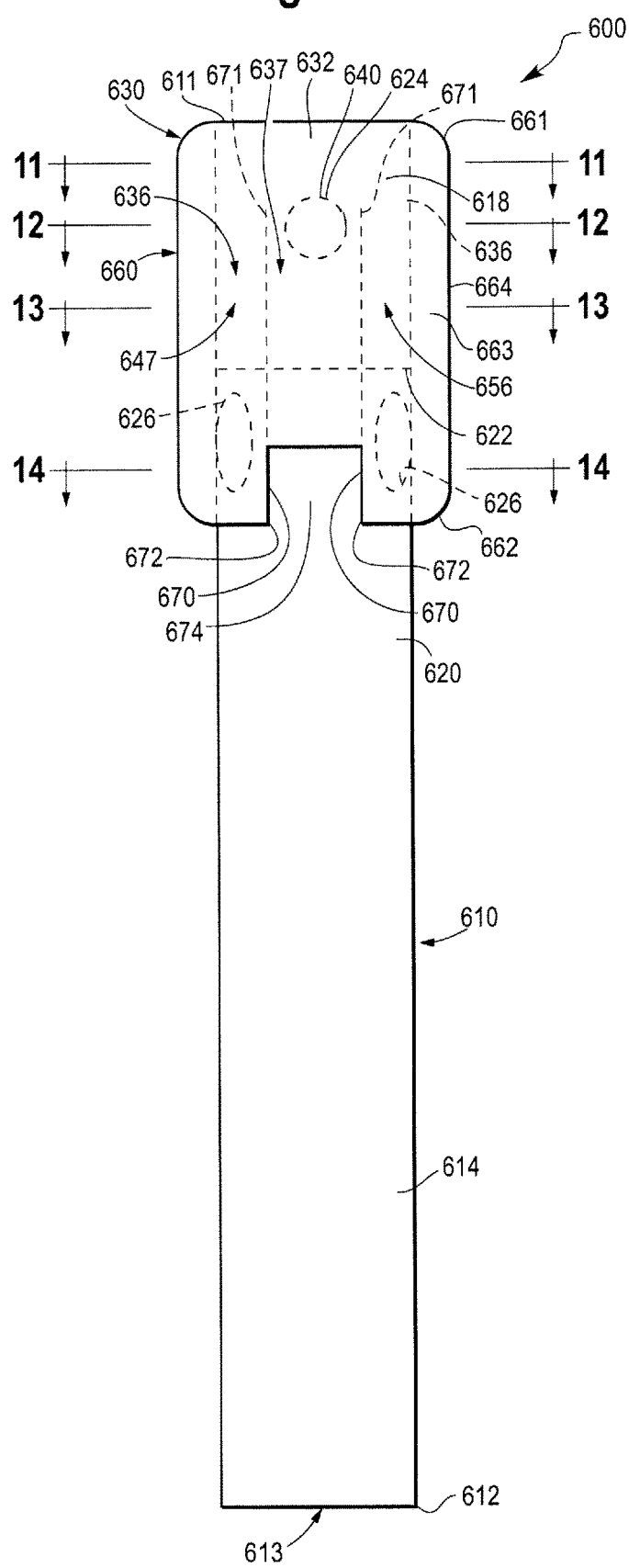

ENDOLUMINAL PROSTHESIS

RELATED APPLICATION

The present application is a divisional of U.S. application Ser. No. 14/136,631, filed Dec. 20, 2013, which claims priority to U.S. Provisional Application Ser. No. 61/747,536 filed on Dec. 31, 2012, the contents of which application is herein incorporated by reference in its entirety.

TECHNICAL FIELD

This disclosure relates to medical devices and more particularly to an endoluminal prosthesis for implantation within a human or animal body for repair of damaged vessels, ducts, or other physiological pathways and methods for delivering and deploying such an endoluminal prosthesis.

BACKGROUND

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture.

One surgical intervention for weakened, aneurysmal, or ruptured vessels involves the use of a prosthetic device or prosthesis to provide some or all of the functionality of the original, healthy vessel, and/or preserve any remaining vascular integrity by replacing a length of the existing vessel wall that spans the site of vessel failure. For example, techniques have been developed for repairing abdominal aortic aneurysms by intraluminally delivering an endovascular graft to the aneurysm site through the use of a catheter-based delivery system. The endovascular grafts typically include a tube of pliable material (e.g., expanded polytetrafluoroethylene (ePTFE) or woven polyester) in combination with a graft anchoring component, which operates to hold the tubular graft in its intended position within the aorta. Most commonly, the graft anchoring component is formed of a stent or frame that is radially expandable to exert outwardly directing radial pressure against the surrounding blood vessel wall. The stent or frame can be either attached to or incorporated into the body of the tubular graft or provided separate from the graft and deployed within the graft.

It is preferable that these prostheses seal off the failed portion of the vessel. For weakened or aneurysmal vessels, even a small leak in the prosthesis may lead to the pressurization of, or flow in, the treated vessel which may aggravate the condition the prosthesis was intended to treat. A prosthesis of this type may be used, for example, to treat aneurysms of the abdominal aortic, iliac, or branch vessels, such as the renal, arteries.

A prosthetic device may be of unitary construction or may include multiple prosthetic modules. Modular systems typically are assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the frictional forces at the overlap region and enhanced by the radial force exerted by the internal prosthetic module on the external prosthetic module where the two overlap. The fit may be further enhanced by stents fixed to the modules at the overlap region.

A prosthetic device including multiple prosthetic modules may be used for placement at a bifurcation or branch of the vasculature. In the case of a bifurcation, one module may be placed in the primary body vessel and one leg of the bifurcation, and another module may be placed in the other leg of the bifurcation. In the case of a branch, one module may be placed in the primary body vessel, and another module may be placed in the branch vessel. Multiple delivery devices may be used to place the different modules used to form the prosthetic device.

In some situations, a bifurcated or branched graft may be mated with an extension graft. For example, a bifurcated graft may be placed at the bifurcation of the common iliac artery into the external iliac artery and the internal iliac artery to treat an iliac aneurysm. The bifurcated graft may include a main pathway for the external iliac artery and a side branch for the internal iliac artery. The bifurcated graft may be mated to an extension graft overlapping a portion of the bifurcated graft, and the overlap may be disposed proximal of the side branch and within the common iliac artery. If the common iliac artery is especially short, there may not be sufficient space for the bifurcated graft and the extension graft to seal properly. Moreover, shortening the overlap between the bifurcated graft and the extension graft may increase the likelihood of type III endoleak or complete separation of the prosthetic device.

SUMMARY

The present embodiments provide an endoluminal prosthesis for implantation within a human or animal body for repair of damaged vessels, ducts, or other physiological pathways and methods for delivering and deploying such an endoluminal prosthesis.

In one example, an endoluminal prosthesis may include a tubular main body and a branch disposed external of the main body. The main body may include a proximal end opening, a distal end opening, a lumen extending between the proximal end opening and the distal end opening, a sidewall, and a fenestration in the sidewall. The branch may include a tubular retrograde branch segment, a tubular antegrade branch segment, and a tubular branch junction. The retrograde branch segment may include an inlet opening fluidly coupled to the fenestration of the main body and an outlet opening fluidly coupled to the branch junction. The outlet opening of the retrograde branch segment may be positioned longitudinally between the proximal end opening and the fenestration of the main body. The antegrade branch segment may include an inlet opening fluidly coupled to the branch junction and an outlet opening positioned longitudinally distal of the inlet opening of the antegrade branch segment. The retrograde branch segment and the antegrade branch segment may be in fluid communication with one another through the branch junction.

In another example, an endoluminal prosthesis may include a tubular main body and a tubular auxiliary body disposed about the main body. The main body may include a proximal end opening, a distal end opening, a main lumen extending between the proximal end opening and the distal end opening, a sidewall, a first fenestration in the sidewall, and a second fenestration in the sidewall positioned distal of the first fenestration. The auxiliary body may include a sidewall, an outlet opening in the sidewall, a first end attached to the main body proximal of the first fenestration, and a second end attached to the main body distal of the second fenestration. A dividing wall may be attached to the sidewall of the main body and the sidewall of the auxiliary body and extending longitudinally at least partially between the first end of the auxiliary body and the second end of the auxiliary body. A cavity may be disposed between the sidewall of the main body and the sidewall of the auxiliary body. The cavity may include a first chamber and a second chamber disposed on opposite sides of the dividing wall and in fluid communication with one another through an opening in the dividing wall. The main lumen may be in fluid communication with the first chamber through the first fenestration. The main lumen may be in fluid communication with the second chamber through the second fenestration. The first chamber may be in fluid communication with a point external of the prosthesis through the outlet opening of the auxiliary body.

In another example, a method of deploying an endoluminal prosthesis may include introducing a delivery device through a first fenestration in a sidewall of a main body of the prosthesis and into a branch junction of the prosthesis. The delivery device may be advanced through the branch junction into an antegrade branch segment fluidly coupled to the branch junction. A branch extension prosthesis may be deployed within the antegrade branch segment with the delivery device. An extension prosthesis may be deployed within the main body of the prosthesis. A distal end of the extension prosthesis may be disposed longitudinally between the first fenestration and a second fenestration in the sidewall of the main body. The prosthesis may include a retrograde branch segment fluidly coupled to each of the second fenestration and the branch junction. The extension prosthesis may seal the first fenestration.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIG. 10 illustrates one example of an endoluminal prosthesis.

FIGS. 11-14 illustrate transverse cross sectional views of the endoluminal prosthesis taken along lines 11-11, 12-12, 13-13, and 14-14, respectively, of FIG. 10.

DETAILED DESCRIPTION OF THE DRAWINGS AND THE PRESENTLY PREFERRED EMBODIMENTS

The present disclosure relates to an endoluminal prosthesis for implantation within a human or animal body for repair of damaged vessels, ducts, or other physiological pathways and methods for delivering and deploying such an endoluminal prosthesis. The embodiments described in this disclosure will be discussed generally in relation to deployment of stent grafts into the aorta, but the disclosure is not so limited and can be applied to other vasculature or other body vessels or lumens.

In the present disclosure, the term "proximal" refers to a direction that is generally closest to the heart during a medical procedure, while the term "distal" refers to a direction that is farthest from the heart during a medical procedure.

Figure 1:
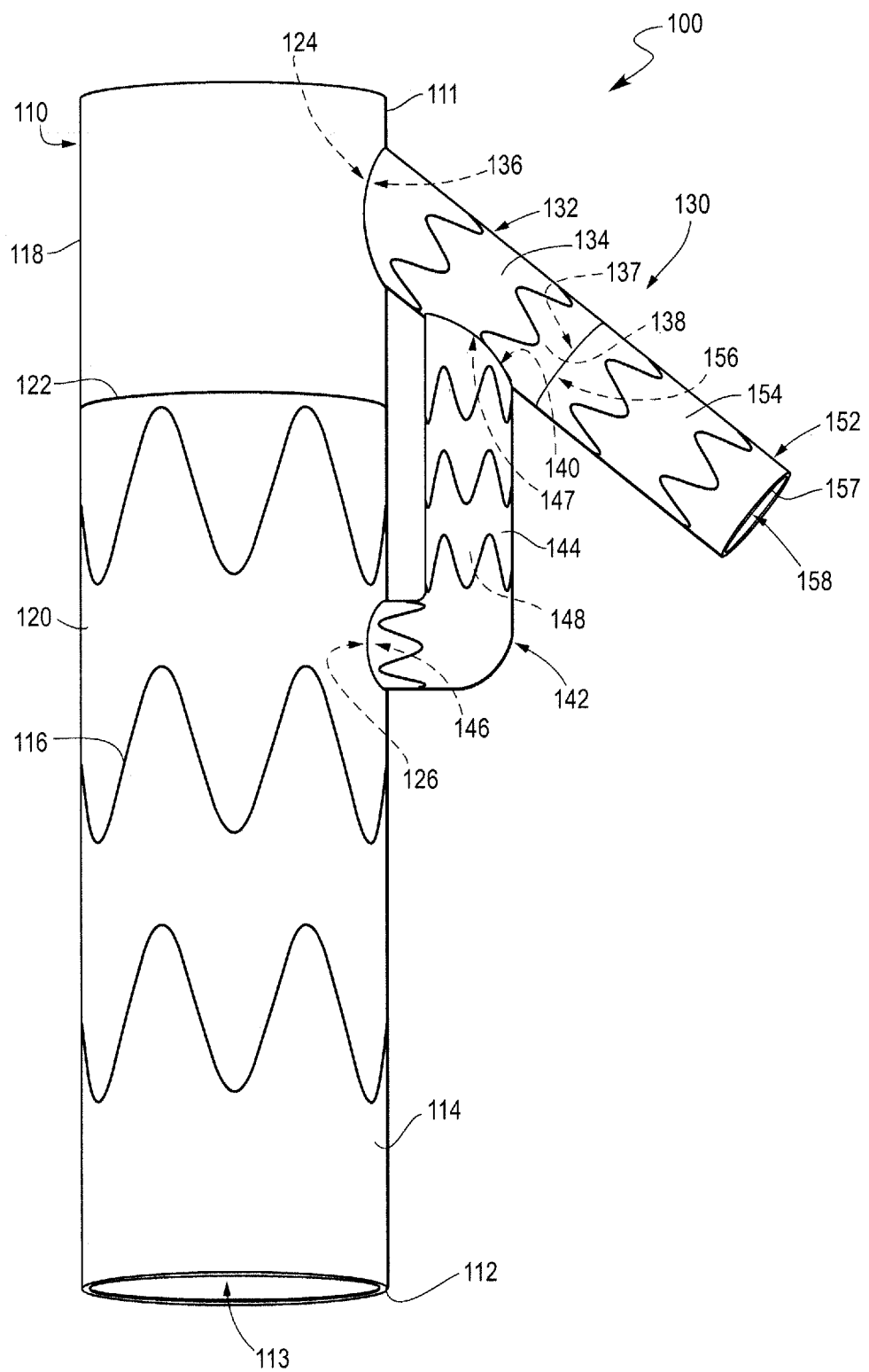
FIG. 1 illustrates one example of an endoluminal prosthesis.

FIG. 1 illustrates one example of an endoluminal prosthesis 100. The prosthesis 100 may be configured for placement at a bifurcation or branch of a body vessel. To that end, the prosthesis 100 may include a main body 110 and a branch 130 attached to the main body. The prosthesis 100 may be configured for placement at a bifurcation of a common iliac artery into an external iliac artery and an internal iliac artery as further described below. To that end, the main body 110 may be configured to extend from the common iliac artery distally into the external iliac artery, and the branch 130 may be configured to extend from the main body toward the internal iliac artery.

The main body 110 may have a proximal end opening at a proximal end 111, a distal end opening at a distal end 112, and a main lumen 113 extending longitudinally within the main body. The main body 110 may be configured as a tubular graft body including a sidewall 114 of a biocompatible graft material. The sidewall 114 may include any suitable biocompatible material known in the art as further described below. The main body 110 may include a support structure 116 attached to the sidewall 114 (e.g., attached to an inner surface and/or an outer surface of the sidewall). The support structure 116 may have any suitable configuration known in the art as further described below.

The prosthesis 100 may include a proximal portion 118 and a distal portion 120. The proximal portion 118 may be a longitudinal segment of the main body 110 positioned near the proximal end 111. For example, the proximal portion 118 may extend longitudinally from the proximal end 111 of the main body 110 to an intermediate point 122 positioned longitudinally between the proximal end 111 and the distal end 112 as shown in FIG. 1. The proximal portion 118 may be configured as a sealing portion to engage an extension prosthesis such that the prosthesis 100 and the extension prosthesis are mated to one another. In other words, at least a portion of the proximal portion 118 may be configured as an overlap region between the prosthesis 100 and an extension prosthesis, which may be deployed within the prosthesis 100 as further described below. The distal portion 120 may be a longitudinal segment of the main body 110 positioned distal of the proximal portion 118. For example, the distal portion 120 may extend longitudinally from the intermediate point 122 of the main body 110 to the distal end 112 as shown in FIG. 1. The distal portion 120 may be configured to remain uncovered by the extension prosthesis deployed within the prosthesis 100 as further described below.

The main body 110 may include a first fenestration such as a proximal fenestration 124 in the sidewall 114 and a second fenestration such as a distal fenestration 126 in the sidewall as shown in FIG. 1. The proximal fenestration 124 may be disposed in the proximal portion 118. The distal fenestration 126 may be disposed in the distal portion 120. The intermediate point 122 of the main body 110 may be positioned longitudinally between the proximal fenestration 124 and the distal fenestration 126 as shown in FIG. 1. The proximal fenestration 124 may be configured to enable cannulation of the branch 130 as further described below. Additionally, or alternatively, the distal fenestration 126 may enable a body fluid (e.g., blood) to flow from the main body 110 into the branch 130 after deployment of the extension prosthesis within the prosthesis 100 also as further described below.

The branch 130 may include a branch junction 132, a retrograde branch segment 142, and an antegrade branch segment 152. The branch junction 132 may be configured as a tubular graft body including a sidewall 134 of a biocompatible graft material. The branch junction 132 may include a first end opening 136 at a first end of the branch junction, a second end opening 137 at a second end of the branch junction, and a lumen 138 extending longitudinally within the branch junction and in communication with each of the first end opening and the second end opening. The first end opening 136 may be fluidly coupled to the proximal fenestration 124 of the main body 110. In other words, the first end of the branch junction 132 may be attached to the sidewall 114 of the main body 110 adjacent to the proximal fenestration 124 such that the first end opening is in fluid communication with the proximal fenestration as shown in FIG. 1. The branch junction 132 may be positioned external of the main body 110 and adjacent to the proximal portion 118. The branch junction 132 may extend outward from the proximal portion 118 of the main body. The first end opening 136 may be configured as a cannulation opening to enable cannulation of the branch 130 through the proximal fenestration 124 of the main body 110 as further described below. The second end opening 137 may be configured as an outlet opening to enable the body fluid to flow from the branch junction 132 into the antegrade branch segment 152 as further described below. The branch junction 132 may include a fenestration 140 in the sidewall 134. The fenestration 140 may be disposed between the first end and the second end of the branch junction 132 as shown in FIG. 1. The fenestration 140 may be configured as an inlet opening to enable the body fluid to flow from the retrograde branch segment 142 into the branch junction 132 as further described below. A portion of the branch junction 132 extending between the first end opening 136 and the fenestration 140 may be configured as a shunt to enable cannulation of the branch junction and/or the antegrade branch segment 152 through the proximal fenestration 124.

The retrograde branch segment 142 may be configured as a tubular graft body including a sidewall 144 of a biocompatible graft material. The retrograde branch segment 142 may include a first end opening 146 at a first end of the retrograde branch segment, a second end opening 147 at a second end of the retrograde branch segment, and a lumen 148 extending longitudinally within the retrograde branch segment and in communication with each of the first end opening and the second end opening. The first end opening 146 may be fluidly coupled to the distal fenestration 126 of the main body 110. In other words, the first end of the retrograde branch segment 142 may be attached to the sidewall 114 of the main body 110 adjacent to the distal fenestration 126 such that the first end opening 146 is in fluid communication with the distal fenestration as shown in FIG. 1. The first end opening 146 may be configured as an inlet opening to enable the body fluid to flow from the main body 110 into the retrograde branch segment 142 as further described below. The second end opening 147 may be fluidly coupled to the fenestration 140 of the branch junction 132. In other words, the second end of the retrograde branch segment 142 may be attached to the sidewall 134 of the branch junction 132 adjacent to the fenestration 140 such that the second end opening 147 is in fluid communication with the fenestration of the branch junction. The second end opening 147 may be configured as an outlet opening to enable the body fluid to flow from the retrograde branch segment 142 into the branch junction 132 as further described below. The retrograde branch segment 142 may extend from the first end toward the proximal end 111 of the main body 110 as shown in FIG. 1. In this manner, the retrograde branch segment 142 may extend from the first end in a direction that is opposite of the natural direction of the flow of body fluid through the body vessel in which the prosthesis 100 is implanted. In other words, the retrograde branch segment 142 may extend in a retrograde direction.

The antegrade branch segment 152 may be configured as a tubular graft body including a sidewall 154 of a biocompatible graft material. The antegrade branch segment 152 may include a first end opening 156 at a first end of the antegrade branch segment, a second end opening 157 at a second end of the antegrade branch segment, and a lumen 158 extending longitudinally within the antegrade branch segment and in communication with each of the first end opening and the second end opening. The first end opening 156 may be fluidly coupled to the second end opening 137 of the branch junction 132. In other words, the first end of the antegrade branch segment 152 may be attached to the second end of the branch junction 132 such that the first end opening 156 of the antegrade branch segment is in fluid communication with the second end opening 137 of the branch junction as shown in FIG. 1. The first end opening 156 may be configured as an inlet opening to enable the body fluid to flow from the branch junction 132 into the antegrade branch segment 152 as further described below. The second end opening 157 may be configured as an outlet opening to enable the body fluid to flow from the antegrade branch segment 152 out of the prosthesis 100 and into a branch extension prosthesis and/or a branch vessel as further described below. The antegrade branch segment 152 may extend from the first end toward the distal end 112 of the main body 110 as shown in FIG. 1. In this manner, the antegrade branch segment 152 may extend from the first end in the natural direction of the flow of body fluid through the body vessel in which the prosthesis 100 is implanted. In other words, the antegrade branch segment 152 may extend in an antegrade direction.

The branch junction 132, the retrograde branch segment 142, and the antegrade branch segment 152 may be aligned with one another with respect to the circumference of the main body 110 as shown in FIG. 1. In this manner, the retrograde branch segment 142 and the antegrade branch segment 152 may be arranged in a stacked configuration in which the retrograde branch segment may be positioned radially between the antegrade branch segment and the main body 110. The antegrade branch segment 152 may be substantially linear as shown in FIG. 1. Alternatively, the antegrade branch segment 152 may be curved (e.g., distally toward the distal end 112 of the main body 110).

The branch junction 132, the retrograde branch segment 142, and the antegrade branch segment 152 may be configured as discrete components attached to one another or as one or more unitary components. For example, the branch junction 132 and the retrograde branch segment 142 may be configured as a unitary member (e.g., a substantially C-shaped member extending between the proximal fenestration 124 and the distal fenestration 126), and the antegrade branch segment 152 may be attached to the unitary branch junction and retrograde branch segment. Alternatively, the branch junction 132 and the antegrade branch segment 152 may be configured as a unitary member (e.g., a substantially straight tube), and the retrograde branch segment 152 may be attached to the unitary branch junction and antegrade branch segment. In other examples, the branch junction 132, the retrograde branch segment 142, and the antegrade branch segment 152 may be formed from a unitary component or any number of discrete components attached to one another to form the branch 130.

The branch 130 (e.g., the branch junction 132, the retrograde branch segment 142, and/or the antegrade branch segment 152) may include a support structure attached to the graft body (e.g., the respective sidewall) as shown in FIG. 1. The support structure may have any suitable configuration known in the art.

Any of the support structures described herein may have any suitable configuration known in the art. For example, the support structures may include one or more stents having any suitable configuration known in the art. The stents may be balloon-expandable or self-expandable. Additionally, or alternatively, the stents may include both balloon expandable and self-expandable portions. The stents may maintain the patency of the prosthesis and/or ensure adequate sealing against the surrounding vascular tissue. Any of the stents mentioned herein may include barbs and/or other anchoring members to help reduce the risk of prosthesis migration. One example of a stent pattern is the Z-stent or Gianturco stent design. Each Z-stent may include a series of substantially straight segments or struts interconnected by a series of bent segments or bends. The bent segments may include acute bends or apices. The Z-stents may be arranged in a zigzag configuration in which the straight segments are set at angles relative to one another and are connected by the bent segments. This design may provide both significant radial force as well as longitudinal support. In tortuous anatomy, branches, or fenestrations, it may be preferable to use alternative stents or modifications to the Z-stent design to avoid stent-to-stent contact. Alternative stent designs may include, for example, annular or helical stents.

Any of the support structures described herein may be made from any suitable material known in the art. In one example, the support structures may be made from standard medical grade stainless steel and may be soldered using silver standard solder (0 lead/0 tin). In other examples, the support structures may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($La_2O_3$), a nickel-titanium alloy, or other suitable materials known in the art. The support structures may be made from nitinol or other superelastic or shape-memory metal. Additionally, or alternatively, the support structures may be configured in a variety of ways to provide a suitable intraluminal support structure. For example, the support structures may include a woven wire structure, a laser-cut cannula, individual interconnected rings, and/or another pattern or design.

In any of the examples described herein, the graft bodies (e.g., the sidewall 114 of the main body 110, the sidewall 134 of the branch junction 132, the sidewall 144 of the retrograde branch segment 142, and/or the sidewall 154 of the antegrade branch segment 152) may be made of any material known in the art. The graft bodies may be made of the same or different materials. Preferably, the graft bodies may be formed from a biocompatible material that is substantially non-toxic in the in vivo environment of its intended use and substantially unrejected by the patient's physiological system (i.e., is non-antigenic). For example, the graft bodies may be made of an expanded polytetrafluoroethylene (ePTFE), polytetrafluoroethylene (PTFE), silicone, polyurethane, polyamide (nylon), polyethylene, polypropylene, polyaramid, polyacrylonitrile, cellulose, or another flexible biocompatible material. Additionally, or alternatively, the graft bodies may be formed from known fabric graft materials (e.g., woven polyester, polyetherurethane, or polyethylene such as an ultra-high molecular weight polyethylene (UHMwPE)). Additionally, or alternatively, materials that are not inherently biocompatible may be subjected to surface modifications to render the materials biocompatible. Examples of surface modifications may include graft polymerization of a biocompatible polymer on the surface, coating of the surface with a crosslinked biocompatible polymer, chemical modification with a biocompatible functional group, or immobilization of a compatibilizing agent (e.g., heparin) or other biocompatible substance. Thus, any fibrous material having sufficient strength to survive in the in vivo environment may be used to form a textile graft, provided the final textile is biocompatible.

Additionally, or alternatively, the graft bodies may include a bioremodelable material such as reconstituted or naturally-derived collagenous materials. Suitable remodelable materials may be provided by collagenous extracellular matrix (ECM) materials possessing biotropic properties. For example, suitable collagenous materials may include ECM materials such as those including submucosa, renal capsule membrane, dermal collagen, dura mater, pericardium, fascia lata, serosa, peritoneum or basement membrane layers, including liver basement membrane. Suitable submucosa materials for these purposes may include, for example, intestinal submucosa including small intestinal submucosa, stomach submucosa, urinary bladder submucosa, and uterine submucosa. Collagenous matrices including submucosa (potentially along with other associated tissues) useful in the present invention may be obtained by harvesting such tissue sources and delaminating the submucosa-containing matrix from smooth muscle layers, mucosal layers, and/or other layers occurring in the tissue source. For additional information as to some of the materials which may be useful in the present invention, and their isolation and treatment, reference may be made, for example, to U.S. Pat. Nos. 4,902,508, 5,554,389, 5,993,844, 6,206,931, and 6,099,567. Non-limiting examples of suitable remodelable materials may include SURGISIS® BIODESIGN™ from Cook Medical (Bloomington, Ind.) or the graft prosthesis material described in U.S. Pat. No. 6,206,931 to Cook et al., which is incorporated herein by reference in its entirety. Additionally, or alternatively, the graft bodies may be made of any of the materials described in U.S. Pat. No. 7,407,509 to Greenberg et al. or U.S. Patent Application Pub. No. 2009/0171451 by Kuppurathanam et al., which are incorporated herein by reference in their entirety.

In one example, the prosthesis may be formed from a relatively thin fabric (e.g., formed from UHMwPE). Such a thin fabric may aid in accommodating for the additional branch structure (e.g., the branch junction and/or the retrograde branch segment) positioned external of the main body of the prosthesis. In other words, such a thin fabric material may aid in reducing the profile of the prosthesis so that the prosthesis may be compressed into a reduced diameter delivery configuration and loaded on an introducer (e.g., within a sheath) in a conventional manner. Additionally, or alternatively, the support structure may be configured as a skeleton structure (e.g., a helical or otherwise-shaped stent structure) to prop open the prosthesis.

Figure 2:
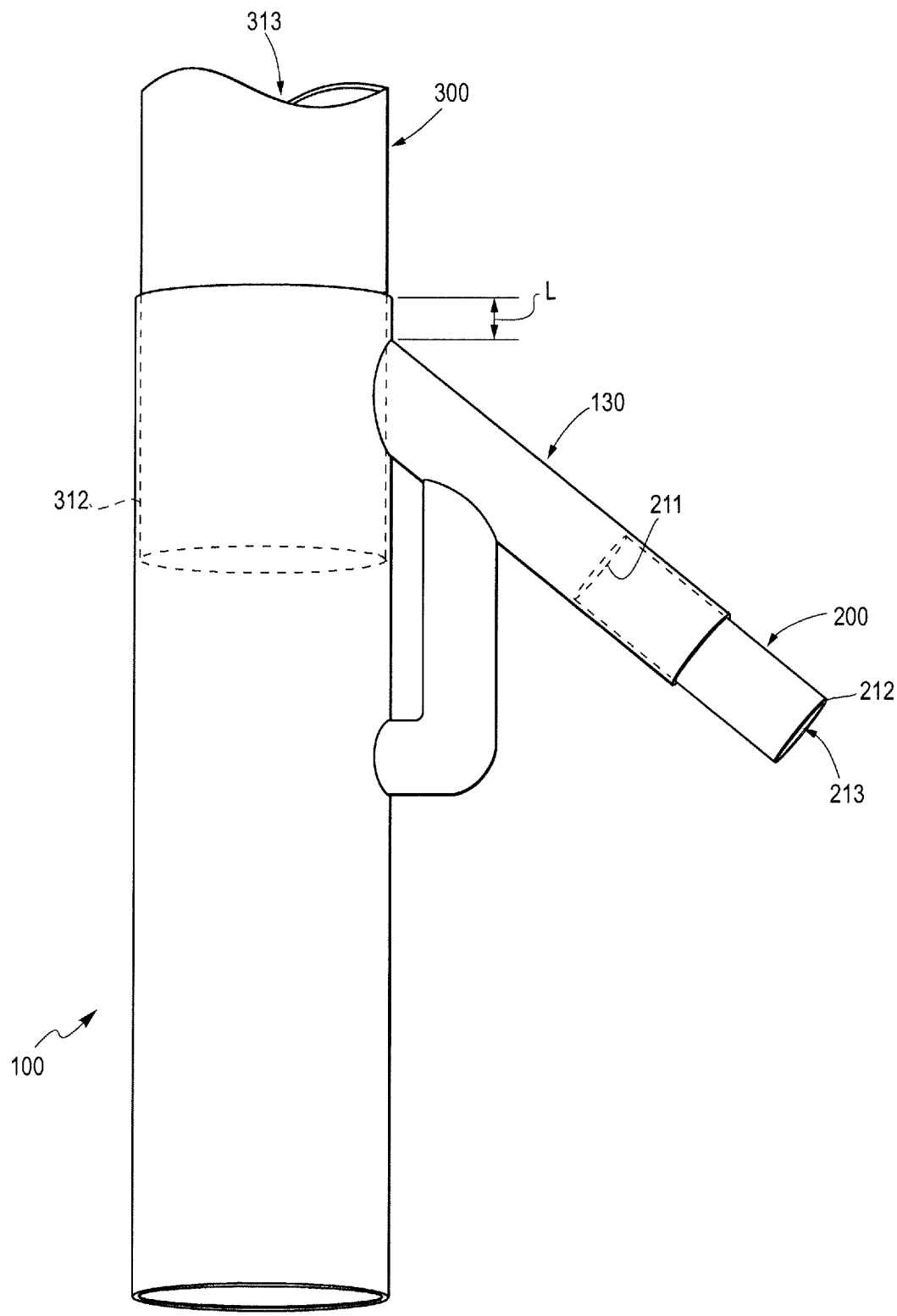
FIG. 2 illustrates the endoluminal prosthesis of FIG. 1 with exemplary extension prostheses deployed therein.

FIG. 2 illustrates the prosthesis 100 with one example of a branch extension prosthesis 200 and one example of a main extension prosthesis 300 deployed therein. The branch extension prosthesis 200 may be deployed within the antegrade branch segment 152 of the branch 130 (e.g., using conventional endovascular techniques). The branch extension prosthesis 200 may be configured as a tubular graft body having a first end 211, a second end 212, and a lumen 213 extending longitudinally within the branch extension prosthesis. The branch extension prosthesis may include a support structure attached to the graft body as described above. The branch extension prosthesis 200 may be deployed within the branch 130 such that the first end 211 is positioned within the antegrade branch segment 152 and the second end 212 is positioned external (e.g., distal) of the antegrade branch segment. In other words, the branch extension prosthesis 200 may be deployed within the branch 130 such that the branch extension prosthesis extends out of the second end opening 158 of the antegrade branch segment 152 as shown in FIG. 2. The branch extension prosthesis 200 may extend from the branch 130 into a branch vessel (e.g., the internal iliac artery) to couple the prosthesis 100 to the branch vessel as further described below.

The main extension prosthesis 300 may be deployed within the main body 110 (e.g., using conventional endovascular techniques). The main extension prosthesis 300 may be configured as a tubular graft body having a first end (not shown), a second end 312, and a lumen 313 extending longitudinally within the main extension prosthesis. The main extension prosthesis may include a support structure attached to the graft body as described above. The main extension prosthesis 300 may be deployed within the main body 110 such that the first end is positioned external (e.g., proximal) of the prosthesis 100 and the second end 312 is positioned within the main body 110. In other words, the main extension prosthesis 300 may be deployed within the main body 110 such that the main extension prosthesis extends into the open proximal end 111 of the main body 110 as shown in FIG. 2. The main extension prosthesis 300 may extend from a body vessel (e.g., an aorta and/or the common iliac artery) into the main body 110 to couple the prosthesis 100 to the body vessel as further described below.

The prosthesis 100 may have a proximal neck length L extending longitudinally between the proximal end 111 of the main body 110 and the proximal fenestration 124. In other words, the neck length L may be the distance between the proximal end 111 of the main body 110 and the branch point (e.g., the proximal fenestration 124 and/or the first end of the branch junction 132) of the prosthesis 100. The branch point of the prosthesis may be the most proximal point at which the branch 130 is attached to the main body 110.

A conventional branched prosthesis includes a main body with a single supply fenestration and a branch fluidly coupled to the supply fenestration and extending from the main body. On such a conventional branched prosthesis, the neck length is at least as long as the desired overlap region between the main extension prosthesis and the conventional branched prosthesis. In other words, the distance between the proximal end of the conventional branched prosthesis and the branch point is sufficient to enable mating of the main extension prosthesis with the conventional branched prosthesis. If the neck length of the conventional branched prosthesis were shorter than the overlap region, the main extension prosthesis would block the flow of body fluid through the supply fenestration and into the branch.

The configuration of the branch 130 of the prosthesis 100 may enable the proximal neck length L to be reduced relative to the conventional branched prosthesis. For example, the supply point of the branch 130 (e.g., the distal fenestration 126 and/or the first end opening 146 of the retrograde branch segment 142) may be distal of the branch point of the prosthesis 100. With the main extension prosthesis 300 deployed in the main body 110 as shown in FIG. 2, the distal end 312 of the main extension prosthesis may be positioned distal of the branch point. In this manner, the overlap region between the main extension prosthesis 300 and the main body 110 may extend distally beyond the branch point. In other words, the proximal neck length L of the prosthesis 100 may be less than the length of the overlap region. In this manner, the proximal neck length L of the prosthesis 100 may be shorter than the proximal neck length of the conventional branched prosthesis while maintaining an overlap region having a length that may be similar to that of the conventional branched prosthesis.

Because the supply point of the branch 130 may be positioned distal of the distal end 312 of the main extension prosthesis 300 (e.g., distal of the proximal portion 118 and/or the intermediate point 122 of the main body 110), the main extension prosthesis may not block the flow of body fluid into the branch 130. In other words, because the supply point of the branch 130 may be positioned distal of the overlap region between the main extension prosthesis 300 and the main body 110, the flow of body fluid from the main body into the branch 130 may be maintained even with the main extension prosthesis deployed within the main body of the prosthesis 100.

The branch 130 may run adjacent to the main body 110 from a supply point (e.g., the distal fenestration 126) to proximal of the intermediate point 122 and then curve (e.g., at the branch junction 132) to run distally toward the branch vessel (e.g., the internal iliac artery) as shown in FIGS. 1-2 and described above. Such a tortuous pathway may be difficult to cannulate, so an auxiliary path to the branch for cannulation may be created using a shunt (e.g., the branch junction 132 or a portion thereof) at the proximal end of the branch 130. The shunt opening (e.g., the first end opening 136 of the branch junction 132) may be disposed in the proximal portion 118 of the main body 110. Once the branch extension prosthesis 200 is placed and the cannula is pulled, as further described below, the shunt opening may be sealed with the main extension prosthesis 300. In other words, because the shunt opening may be positioned within the proximal portion 118 (e.g., the overlap region between the main extension prosthesis 300 and the main body 110), the main extension prosthesis deployed within the main body 110 of the prosthesis 100 may seal or block the flow of body fluid through the shunt opening as shown in FIG. 2.

With the main extension prosthesis 300 deployed in the main body 110 of the prosthesis 100, the body fluid may enter the lumen 113 of the main body through the proximal end 111 and flow distally to the distal fenestration 126. The body fluid may be prevented from flowing through the proximal fenestration 124 and into the lumen 138 of the branch junction 132 by the main extension prosthesis 300, which may block or seal the proximal fenestration. The body fluid may flow through the distal fenestration 126 and into the retrograde branch segment 142. The body fluid may flow through the retrograde branch segment 142 in the retrograde direction and into the branch junction 132. The body fluid may flow through the branch junction 132 and into the antegrade branch segment 152. The body fluid may be prevented from back flowing through the proximal fenestration 124 and into the lumen 113 of the main body 110 by the main extension prosthesis 300, which may block or seal the proximal fenestration. The body fluid may flow through the antegrade branch segment 152 in the antegrade direction and exit the prosthesis 100 through the second end opening 157 of the antegrade branch segment.

FIGS. 3-6 illustrate exemplary method steps for deploying the prosthesis 100 at a bifurcation of a common iliac artery 410 into an external iliac artery 412 and an internal iliac artery 414. Although the prosthesis 100 is described herein as being configured for placement in the iliac arteries, this disclosure is not so limited. The prosthesis may be configured for placement at any other bifurcation or branch within any other body vessel. For example, the prosthesis may be configured for placement at a bifurcation such as the aortic bifurcation; at a branch such as the renal arteries, the celiac artery, the superior mesenteric artery, the innominate artery, the carotid artery, or the subclavian artery; or any other bifurcation or branch at which multiple body vessels are joined to one another.

Figure 3:
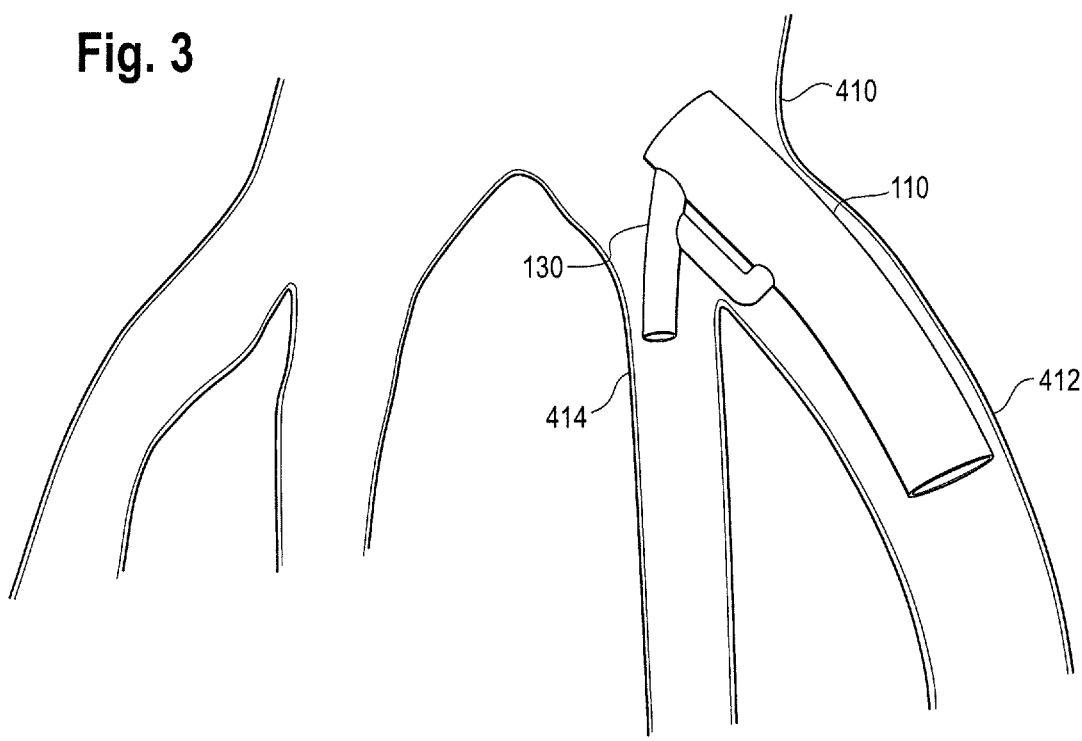
FIG. 3 illustrates the endoluminal prosthesis of FIG. 1 deployed within a body vessel.

The prosthesis 100 may be delivered to the common iliac artery 410 using any suitable delivery device or introducer known in the art. For example, the prosthesis 100 may be compressed into a reduced diameter delivery configuration and loaded onto the introducer. The proximal tip of the introducer may be advanced proximally over a guide wire through a femoral artery and into the common iliac artery 410. With the introducer in position, the prosthesis 100 may be deployed (e.g., by withdrawing a sheath and/or by manipulating one or more trigger wires of the introducer). Upon deployment, the prosthesis 100 may expand from the delivery configuration to an expanded configuration to engage inner walls of the common iliac artery 410 and the external iliac artery 412 as shown in FIG. 3. The main body 110 of the prosthesis 100 may be positioned within the common iliac artery 410 and the external iliac artery 412. The branch 130 of the prosthesis 100 may extend toward the internal iliac artery 414. For clarity, FIGS. 3-6 show a space remaining between the prosthesis 100 and the inner walls of the body vessels. However, the prosthesis 100 may be sized such that, upon deployment, the prosthesis engages the inner walls of the body vessels.

The branch 130 (e.g., the branch junction 132, the retrograde branch segment 142, and/or the antegrade branch segment 152) may include a support structure as described above. The support structure may aid in maintaining the lumen of the branch 130 (e.g., the lumen 138, the lumen 148, and/or the lumen 158) open to enable the body fluid to flow through the branch. For example, the retrograde branch segment 142 may be positioned between the inner wall of the internal iliac artery 414 and the main body 110 of the prosthesis 100 as shown in FIG. 3. The retrograde branch segment 142 may include a support structure to prevent the retrograde branch segment from being collapsed (e.g., by the radially outward force of the main body 110).

Figure 4:
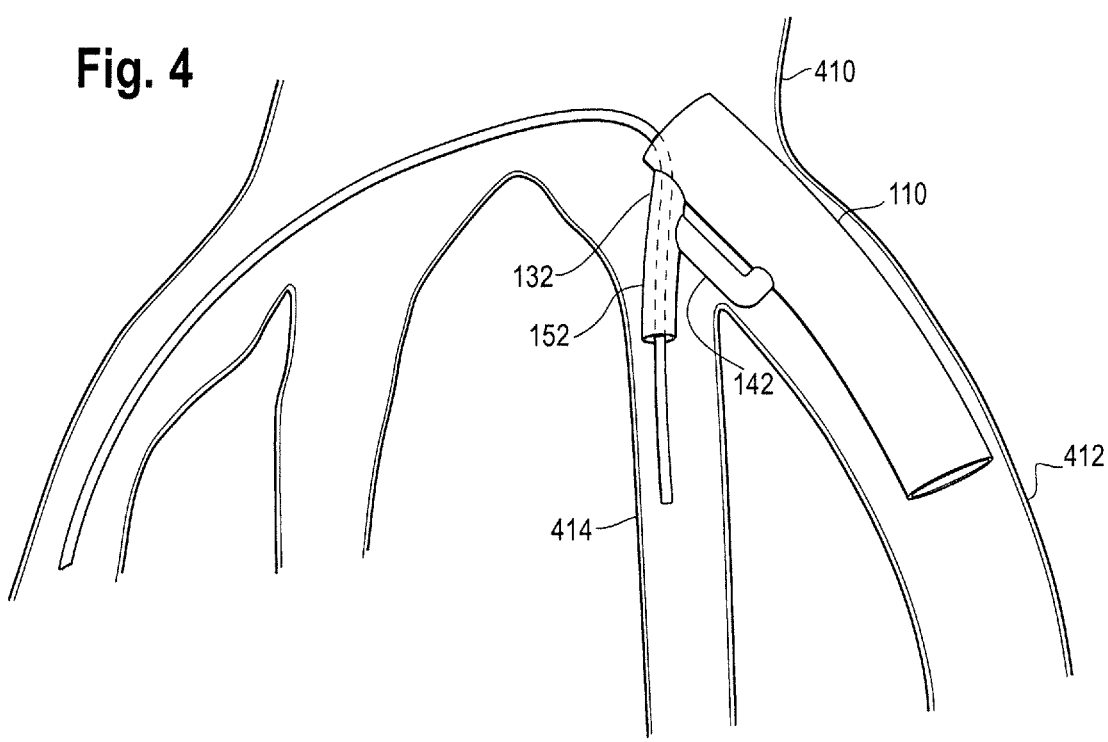
FIGS. 4-5 illustrate deployment of an exemplary branch extension prosthesis within the endoluminal prosthesis deployed within the body vessel as shown in FIG. 3.

A second introducer may be used to cannulate the branch 130 of the prosthesis 100 as shown in FIG. 4. The second introducer may be advanced to a second common iliac artery (e.g., through a second femoral artery), over an aortic bifurcation, and into the lumen 113 of the prosthesis 100 through the proximal end 111. The second introducer may be advanced into the branch junction 132 via the proximal fenestration 124 and the first end opening 136. The second introducer may be further advanced out of the branch 130 via the antegrade branch segment 154 and into the internal iliac artery 414 as shown in FIG. 4. By cannulating the antegrade branch segment 152 through the proximal fenestration 124 of the main body 110 and the branch junction 132, it may be unnecessary to navigate the second introducer through the relatively tortuous pathway extending from the distal fenestration 126 through the retrograde branch segment 142, turning into the branch junction, and extending further into the antegrade branch segment 152. The branch junction 132 and the antegrade branch segment 152 may provide a substantially non-tortuous pathway from the proximal fenestration 124 to the second end opening 158 of the antegrade branch segment to aid in cannulating the branch 130 with the second introducer.

Figure 5:
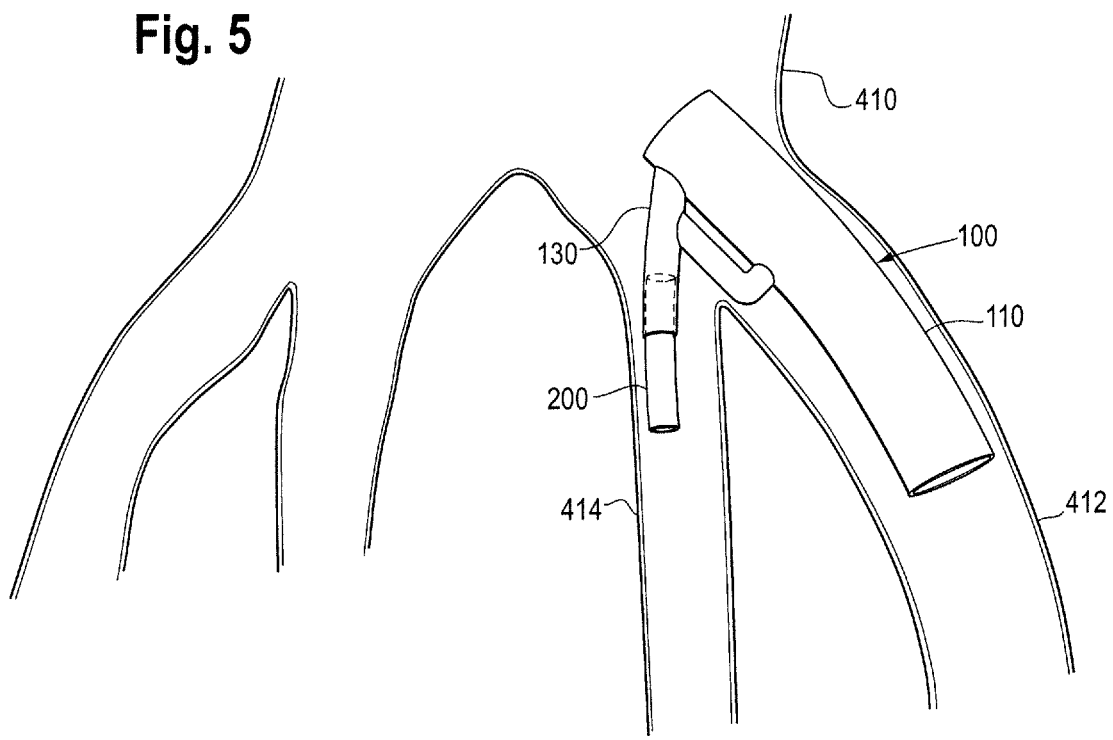

The branch extension prosthesis 200 may be deployed within the branch 130 and the internal iliac artery 414 using the second introducer. The branch extension prosthesis 200 may extend from the antegrade branch segment 152 into the internal iliac artery 414 to couple the prosthesis 100 to the internal iliac artery as shown in FIG. 5.

Figure 6:
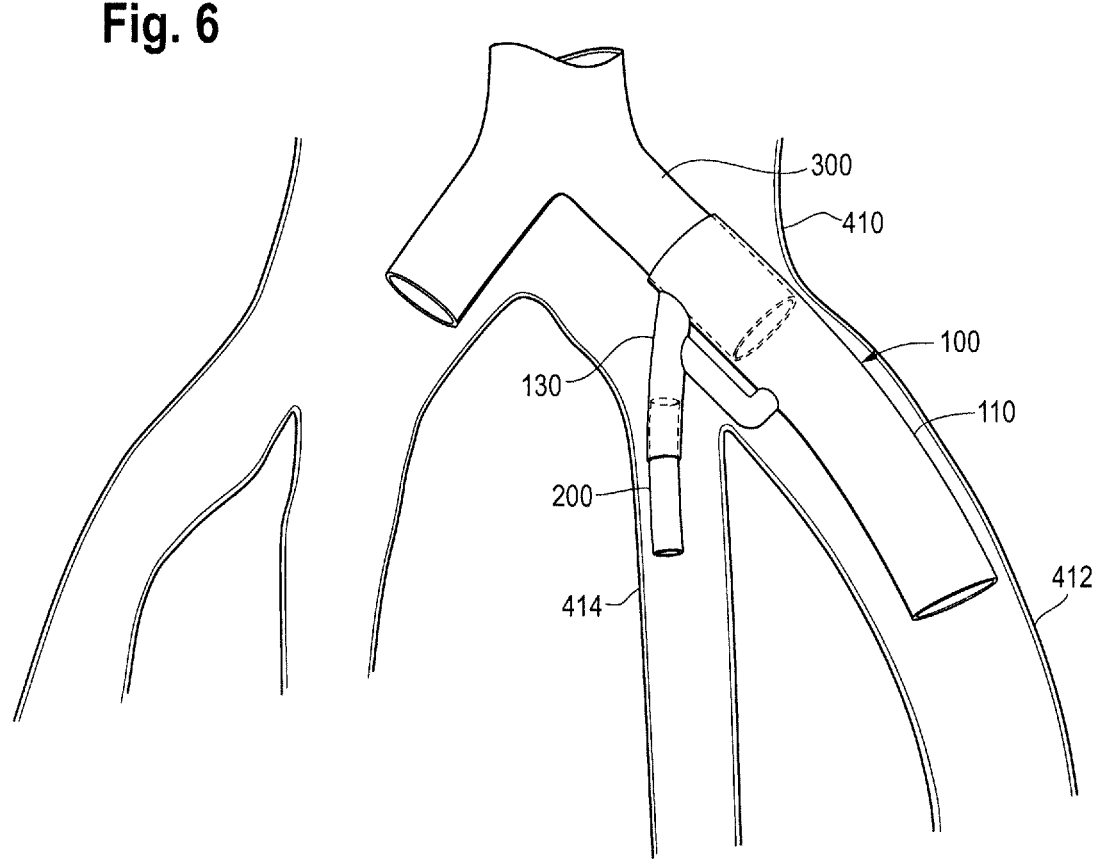
FIG. 6 illustrates an exemplary main extension prosthesis deployed within the endoluminal prosthesis deployed within the body vessel as shown in FIG. 4.

The main extension prosthesis 300 may be delivered and deployed within the main body 110 of the prosthesis 100 as shown in FIG. 6. The main extension prosthesis 300 may be compressed into a reduced diameter delivery configuration and loaded onto a third introducer. The third introducer may be advanced into the aorta to a position proximal of the common iliac artery 410. With the third introducer in position, the main extension prosthesis 300 may be deployed (e.g., by withdrawing a sheath and/or by manipulating one or more trigger wires of the introducer). The main extension prosthesis 300 may be deployed within the main body 110 of the prosthesis 100 such that the distal end 312 of the main extension prosthesis overlaps the proximal end 111 of the main body 110 along at least a portion of the proximal portion 118. The main extension prosthesis 300 and the main body 110 of the prosthesis 100 may be mated as described above with reference to FIG. 2.

The main extension prosthesis 300 may have any suitable configuration known in the art. For example, the main extension prosthesis 300 may be configured as a bifurcated prosthesis as shown in FIG. 6. The main body of the main extension prosthesis 300 may be positioned within the aorta, and the legs of the main extension prosthesis may be positioned within each of the common iliac arteries. In this manner, the main extension prosthesis 300 may span the aortic bifurcation as shown in FIG. 6. In other examples, the main extension prosthesis may have a non-bifurcated configuration.

In some patients, the common iliac artery 410 may be relatively short compared to a typical common iliac artery. In such patients, one leg of the main extension prosthesis 300 may extend distally to the bifurcation of the common iliac artery 410 as shown in FIG. 6. Mating a conventional branched prosthesis with the main extension prosthesis in such a situation will result in either the supply point of the branch being blocked by the main extension prosthesis or the branch being positioned distal of the bifurcation. In either case, the conventional branch prosthesis will not fit properly in the space available.

The prosthesis 100 may have a relatively short proximal neck length L as described above with reference to FIG. 2. Additionally, or alternatively, the proximal portion 118 of the prosthesis 100 may extend distally beyond the branch point, and the supply point of the prosthesis 100 may be positioned distal of the proximal portion also as described above with reference to FIG. 2. In this manner, the prosthesis 100 may be capable of mating with the main extension prosthesis 300 with the branch 130 properly aligned with the internal iliac artery 414 and without blocking the supply point as shown in FIG. 6. In this manner, the prosthesis 100 may be configured for use in patients having relatively short common iliac arteries. For example, the supply point of the prosthesis 100 may be positioned distal of the bifurcation of the common iliac artery 410. The configuration of the branch 130 may enable the body fluid to flow in a retrograde direction (e.g., through the retrograde branch segment 142) to a position proximal of the bifurcation (e.g., to the branch junction 132) and then in an antegrade direction (e.g., through the antegrade branch segment 152) toward the internal iliac artery 414 as shown in FIG. 6. In this manner, a sufficient overlap between the main extension prosthesis 300 may be provided while maintaining proper alignment of the branch 130 with the branch vessel.

Figure 7:
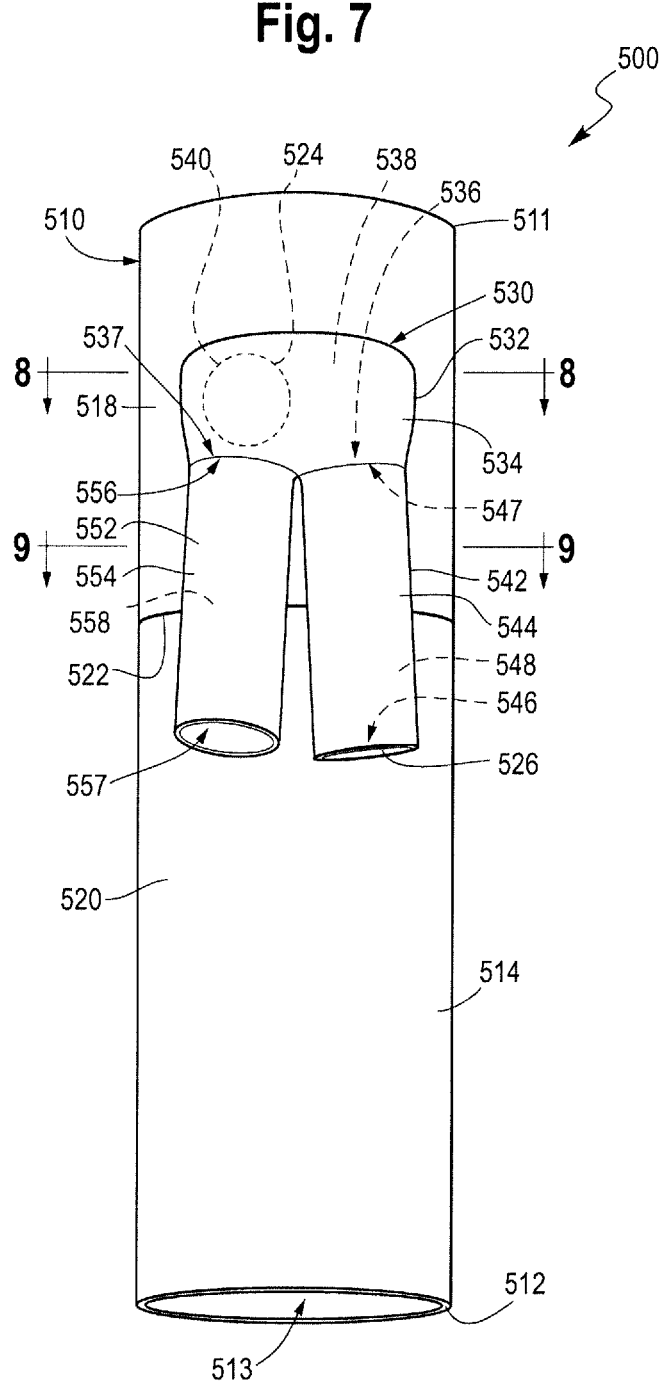
FIG. 7 illustrates one example of an endoluminal prosthesis.
Figure 8:
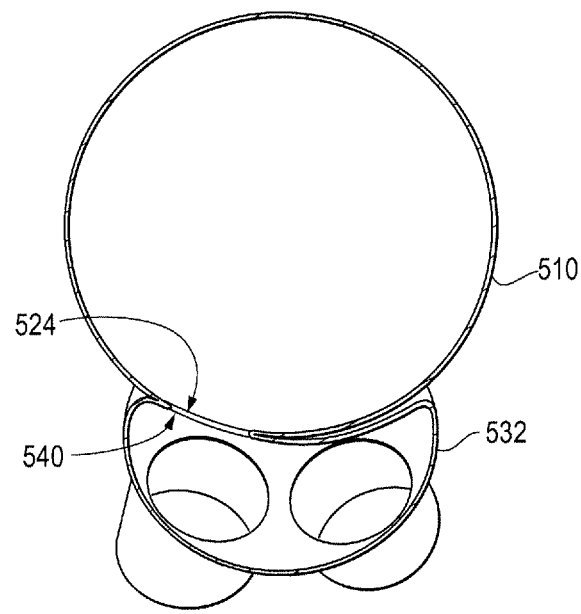
FIGS. 8-9 illustrate transverse cross sectional views of the endoluminal prosthesis taken along lines 8-8 and 9-9, respectively, of FIG. 7.
Figure 9:
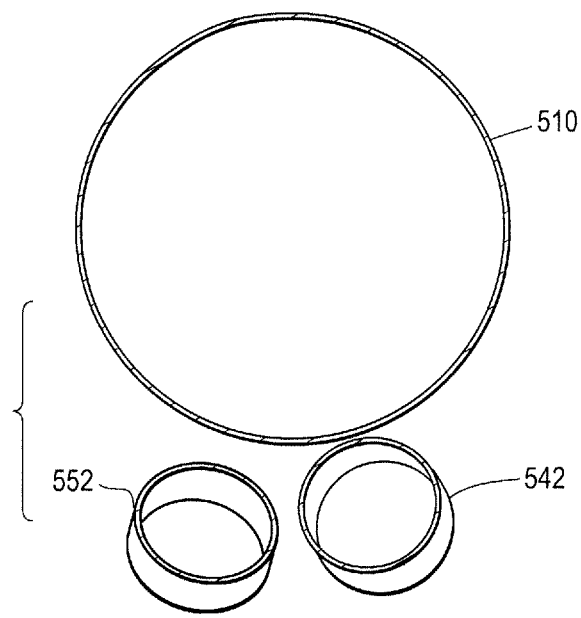

FIG. 7 illustrates one example of an endoluminal prosthesis 500. FIGS. 8 and 9 illustrate transverse cross sectional views of the prosthesis 500 taken along lines 8-8 and 9-9, respectively, of FIG. 7. The prosthesis 500 may be configured substantially as described above with reference to the prosthesis 100 except for the differences described below. For example, the prosthesis 500 may include a main body 510 and a branch 530 attached to the main body. The main body 510 may have a proximal end opening at a proximal end 511, a distal end opening at a distal end 512, and a main lumen 513 extending longitudinally within the main body. The main body 510 may be configured as a tubular graft body including a sidewall 514 and a support structure (not shown) attached to the sidewall 514.

The prosthesis 500 may include a proximal portion 518 positioned proximal of an intermediate point 522 and a distal portion 520 positioned distal of the intermediate point as shown in FIG. 7. The proximal portion 518 may be configured to engage an extension prosthesis (e.g., the main extension prosthesis 300) as described above with reference to the prosthesis 100. The main body 510 may include a proximal fenestration 524 in the sidewall 514 and a distal fenestration 526 in the sidewall. The proximal fenestration 524 may be disposed in the proximal portion 518, and the distal fenestration 526 may be disposed in the distal portion 520 as described above with reference to the prosthesis 100.

The branch 530 may include a branch junction 532, a retrograde branch segment 542, and an antegrade branch segment 552. The branch junction 532 may be configured as a tubular graft body including a sidewall 534 of a biocompatible graft material. The branch junction 532 may include a first end opening 536 at a first end of the branch junction, a second end opening 537 at a second end of the branch junction, and a lumen 538 extending longitudinally within the branch junction. The first end opening 536 may be fluidly coupled to the second end opening 547 of the retrograde branch segment 542 as shown in FIG. 7. The first end opening 536 may be configured as an inlet opening to enable the body fluid to flow from the retrograde branch segment 142 into the branch junction 532. The second end opening 537 may be fluidly coupled to the first end opening 556 of the antegrade branch segment 552 as shown in FIG. 7. The second end opening 537 may be configured as an outlet opening to enable the body fluid to flow from the branch junction 532 into the antegrade branch segment 552. The branch junction 532 may include a fenestration 540 in the sidewall 534. The fenestration 540 may be fluidly coupled to the proximal fenestration 524 of the main body 510 as shown in FIGS. 7-8. In this manner, the fenestration 540 may be configured as a cannulation opening to enable cannulation of the branch 530 through the proximal fenestration 524 of the main body 510.

The retrograde branch segment 542 may be configured as a tubular graft body including a sidewall 544 of a biocompatible graft material. The retrograde branch segment 542 may include a first end opening 546 at a first end of the retrograde branch segment, a second end opening 547 at a second end of the retrograde branch segment, and a lumen 548 extending longitudinally within the retrograde branch segment. The first end opening 546 may be fluidly coupled to the distal fenestration 526 of the main body 510. The first end opening 546 may be configured as an inlet opening to enable the body fluid to flow from the main body 510 into the retrograde branch segment 542. The second end opening 547 may be fluidly coupled to the first end opening 536 of the branch junction 532. The second end opening 547 may be configured as an outlet opening to enable the body fluid to flow from the retrograde branch segment 542 into the branch junction 532. The retrograde branch segment 542 may extend in a retrograde direction as described above with reference to the prosthesis 100.

The antegrade branch segment 552 may be configured as a tubular graft body including a sidewall 554 of a biocompatible graft material. The antegrade branch segment 552 may include a first end opening 556 at a first end of the antegrade branch segment, a second end opening 557 at a second end of the antegrade branch segment, and a lumen 558 extending longitudinally within the antegrade branch segment. The first end opening 556 may be fluidly coupled to the second end opening 537 of the branch junction 532. The first end opening 556 may be configured as an inlet opening to enable the body fluid to flow from the branch junction 532 into the antegrade branch segment 552. The second end opening 557 may be configured as an outlet opening to enable the body fluid to flow from the antegrade branch segment 552 out of the prosthesis 500 and into a branch extension prosthesis and/or a branch vessel. The antegrade branch segment 552 may extend in an antegrade direction as described above with reference to the prosthesis 100.

The branch 530 may be configured as a substantially U-shaped tubular member as shown in FIG. 7. To that end, the branch junction 532 may be configured as a curve of the U-shaped branch 530, and each of the retrograde branch segment 542 and the antegrade branch segment 552 may be configured as a leg of the U-shaped branch. In this manner, the first end opening 536 and the second end opening 537 of the branch junction 532 may be positioned adjacent to one another. The retrograde branch segment 542 and the antegrade branch segment 552 may be misaligned with one another with respect to the circumference of the main body 510. For example, the retrograde branch segment 542 and the antegrade branch segment 552 may be positioned adjacent to one another and to the main body (e.g., in a side-by-side configuration) as shown in FIGS. 7 and 9. In this manner, the profile or outside diameter of the prosthesis 500 may be reduced relative to the stacked configuration described above with reference to FIGS. 1-2. For example, because each of the retrograde branch segment 542, the branch junction 532, and the antegrade branch segment 552 may be positioned adjacent to the main body 510, the profile of the prosthesis 500 may be reduced.

The sidewall 534 of the branch junction 532 may be attached to the sidewall 514 of the main body 510 to fluidly couple the fenestration 540 of the branch junction to the proximal fenestration 524 of the main body as shown in FIGS. 7-8. Alternatively, a tubular shunt may extend between the branch junction 532 and the main body 510 to fluidly couple the fenestration 540 of the branch junction to the proximal fenestration 524 of the main body.

The prosthesis 500 may be deployed generally as described above with reference to FIGS. 3-6. For example, to cannulate the branch 530, an introducer may be advanced into the branch junction 532 via the proximal fenestration 524 and the fenestration 540 and then further advanced out of the branch 530 via the antegrade branch segment 552. The branch extension prosthesis 200 may be deployed within the antegrade branch segment 552 using the introducer. The main extension prosthesis 300 may be deployed within the prosthesis 500. Upon deployment of the main extension prosthesis 300, the proximal fenestration 524 may be sealed by the overlap between the main extension prosthesis and the main body 510 of the prosthesis 500.

With the prosthesis 500 deployed within the body vessel, the body fluid may flow through the lumen 513 of the main body 510 in the antegrade direction to the distal fenestration 526. The body fluid may flow through the distal fenestration 526 into the retrograde branch segment 542 and in the retrograde direction to the second end opening 547. The body fluid may be redirected from the retrograde direction to the antegrade direction while flowing through the branch junction 532 from the first end opening 536 to the second end opening 537. The body fluid may flow through the second end opening 537 into the antegrade branch segment 552 and in the antegrade direction to the second end opening 557.

The position of the supply point (e.g., the first end opening 546) of the branch 530 distal of the overlap region between the main extension prosthesis 300 and the main body 510 may enable the prosthesis 500 to have a reduced neck length as described above with reference to FIGS. 1-2. In this manner, the prosthesis 500 may be configured for placement within a patient having a relatively short common iliac artery as described above with reference to the prosthesis 100.

FIG. 10 illustrates one example of an endoluminal prosthesis 600. FIGS. 11-14 illustrate transverse cross sectional views of the prosthesis 600 taken along lines 11-11, 12-12, 13-13, and 14-14, respectively, of FIG. 10. The prosthesis 600 may include a main body 610 and a branch 630 attached to the main body. The main body 610 may have a proximal end opening at a proximal end 611, a distal end opening at a distal end 612, and a main lumen 613 extending longitudinally within the main body. The main body 610 may be configured as a tubular graft body including a sidewall 614 and a support structure (not shown) attached to the sidewall 614.

The main body 610 of the prosthesis 600 may include a proximal portion 618 positioned proximal of an intermediate point 622 and a distal portion 620 positioned distal of the intermediate point as shown in FIG. 10. The proximal portion 618 may be configured to engage an extension prosthesis. For example, the main extension prosthesis 300 may be deployed within the main body 610 as described above with reference to the prosthesis 100. The main body 610 may include a proximal fenestration 624 in the sidewall 614 and a distal fenestration 626 in the sidewall. In one example, the prosthesis 600 may include two distal fenestrations 626 spaced from one another about the circumference of the sidewall 614 as shown in FIG. 10 and further described below. The proximal fenestration 624 may be disposed in the proximal portion 618, and the distal fenestration 626 may be disposed in the distal portion 620. In this manner, the extension prosthesis (e.g., the main extension prosthesis 300) may overlap at least a portion of the proximal portion 618 of the main body 610 without blocking the distal fenestration 626 as described above with reference to the prosthesis 100.

The prosthesis 600 may include an auxiliary body 660 disposed about the main body 610 as shown in FIGS. 10-14. The branch 630 of the prosthesis 610 may be defined between the main body 610 and the auxiliary body 660 as further described below. The auxiliary body 660 may have a first end 661, a second end 662, and an auxiliary lumen 663 extending longitudinally within the auxiliary body. The auxiliary body 660 may be configured as a tubular graft body including a sidewall 664 and a support structure (not shown) attached to the sidewall 664. The sidewall 664 may extend radially inward at the first end 661 and/or the second end 662 of the auxiliary body as shown in FIG. 10 to engage the sidewall 614 of the main body 610 as further described below. In this manner, the first end 661 and/or the second end 662 of the auxiliary body 660 may be configured as an end wall attached to the main body 610.

The main body 610 may be received within the auxiliary lumen 663 of the auxiliary body 660 as shown in FIGS. 10-14. In this manner, the auxiliary body 660 may be configured as a tubular member disposed about a proximal portion of the main body 610. The first end 661 of the auxiliary body 660 may be attached to the sidewall 614 of the main body 610 along the proximal portion 618. For example, the first end 661 of the auxiliary body 660 may be attached to the first end 611 of the main body 610 as shown in FIG. 10. The second end 662 of the auxiliary body 660 may be attached to the sidewall 614 of the main body 610 along the distal portion 620. For example, the second end 662 of the auxiliary body 660 may be attached to the main body 610 at a point distal of the distal fenestration 626 as shown in FIG. 10. The first end 661 and/or the second end 662 of the sidewall 664 may extend radially inward from an intermediate portion of the sidewall 664 so that the intermediate portion of the sidewall 664 of the auxiliary body 660 is spaced radially from the sidewall 614 of the main body 610. In this manner, a cavity 628 may be defined between the sidewall 614 of the main body 610 and the sidewall 664 of the auxiliary body 660 between the first end 661 and the second end 662 of the auxiliary body as shown in FIGS. 10-14. The first end 661 and the second end 662 of the auxiliary body 660 may be sealably attached to the sidewall 614 of the main body 610 (e.g., by suturing or bonding). In this manner, the body fluid disposed in the cavity 628 may be substantially prevented from escaping except through the outlet opening 674 of the antegrade branch segment 652 as further described below.

The proximal fenestration 624 and the distal fenestration 626 of the main body 610 may be positioned within the auxiliary body 660. The sidewall 664 of the auxiliary body 660 may be attached to the sidewall 614 of the main body 610 at one or more circumferential and/or longitudinal positions. For example, a posterior region of the sidewall 664 of the auxiliary body 660 may be attached to a posterior region of the sidewall 614 of the main body 610 as shown in FIGS. 11-14. The posterior region of the auxiliary body 660 may be configured as a circumferential segment of the sidewall 664 extending longitudinally along a posterior side of the auxiliary body. Additionally, or alternatively, the posterior region of the main body 610 may be configured as a circumferential segment of the sidewall 614 extending longitudinally along a posterior side of the main body. The main body 610 may be offset or non-centered within the auxiliary body 660. In other words, the main body 610 and the auxiliary body 660 may not be coaxial. In this manner, the sidewall 664 of the auxiliary body 660 and the sidewall 614 of the main body 610 may be attached to one another along the posterior regions and spaced from one another along anterior regions disposed substantially opposite the posterior regions with respect to the circumference of the respective auxiliary body or main body. In other words, the main body 610 and the auxiliary body 660 may be attached to one another along their respective posterior sides and spaced from one another along their respective anterior sides.

The cavity 628 may be defined within the lumen 663 of the auxiliary body 660 between the sidewall 614 of the main body 610 and the sidewall 664 of the auxiliary body. The cavity 628 may be divided into a plurality of chambers to form the branch junction 632, the retrograde branch segment 642, and the antegrade branch segment 652 of the branch 630 as further described below. To that end, the prosthesis 600 may include one or more dividing walls 670 disposed in the cavity 628. The dividing walls 670 may divide the cavity 628 into two or more chambers as further described below. In one example, the prosthesis 600 may include two dividing walls 670 as shown in FIG. 10. In other examples, the prosthesis may include any number of dividing walls to divide the cavity into any number of chambers.

Each dividing wall 670 may extend longitudinally within the cavity 628 and radially between the sidewall 614 of the main body 610 and the sidewall 664 of the auxiliary body 660. Each dividing wall 670 may be attached to the sidewall 614 of the main body 610 and the sidewall 664 of the auxiliary body 660. In other words, the sidewall 614 of the main body 610 and the sidewall 664 of the auxiliary body 660 may be joined to one another by the dividing walls 670. Each dividing wall 670 may separate a chamber positioned on one side of the dividing wall from a chamber positioned on an opposite side of the dividing wall. Each chamber may be in fluid communication with an adjacent chamber through an opening in the dividing wall 670. Each dividing wall 670 may have a first end 671 and a second end 672. The first end 671 of the dividing wall 670 may be spaced longitudinally from the first end 661 of the auxiliary body 660. The opening in the dividing wall may be configured as a longitudinal space or gap between the first end 671 of the dividing wall and the first end 661 of the auxiliary body. Alternatively, the first end of the dividing wall may be attached to the first end of the auxiliary body. Additionally, or alternatively, the opening in the dividing wall may be configured as a fenestration in the dividing wall. The second end 672 of the dividing wall 670 may be attached to the second end 662 of the auxiliary body 660. The branch junction 632 may extend from the first end 661 of the auxiliary body 660 distally beyond the first ends 671 of the dividing walls 670 to join the chambers to one another near the first end of the auxiliary body as further described below. The first end 671 of each dividing wall 670 may be positioned longitudinally between the first end 661 of the auxiliary body 660 and the proximal fenestration 624 of the main body 624 as shown in FIG. 10. This may aid in cannulating the antegrade branch segment 652 through the proximal fenestration 624 (e.g., by guiding an introducer between the dividing walls and out of the antegrade branch segment 652) as further described below.

In one example, the auxiliary body 660 may include a support structure attached to the sidewall 664. The support structure of the auxiliary body 660 may be configured as described above with reference to the support structure 116 of the prosthesis 100 (e.g. as one or more stents). The proximal portion 618 of the main body 610 may be unstented or substantially free of a support structure. The support structure of the auxiliary body 660 may exert a radially outward force (e.g., an expansive force) on the auxiliary body. The auxiliary body 660 may be attached to the main body 610 by the dividing walls 670 as described above. In this manner, the support structure of the auxiliary body 660 may exert a radially outward force on the main body 610. In other words, the expansive force of the support structure may urge the auxiliary body 660 toward an expanded configuration, which may pull radially outward on the dividing walls to urge the main body 610 outward toward an expanded configuration. In this manner, the support structure may be omitted from the portion of the main body 610 disposed within the auxiliary body. This may aid in reducing the profile of at least a portion of the prosthesis 600. Additionally, or alternatively, the portion of the main body 610 disposed external of the auxiliary body 660 may include the support structure. This may aid in providing support and/or radially expansive force to the portion of the main body disposed external of the auxiliary body 660. In other examples, any portion of the main body may include the support structure.

The branch 630 of the prosthesis 600 may be cooperatively defined by the main body 610, the auxiliary body 660, and the dividing walls 670. For example, the branch junction 632 may include a portion of the cavity 628 that is positioned longitudinally adjacent to the proximal fenestration 624 of the main body 610. The branch junction 632 may extend between the first end 661 of the auxiliary body 660 and a position longitudinally between the proximal fenestration 624 and the distal fenestration 626. The first end 671 of each dividing wall 670 may be positioned longitudinally within the branch junction 632. The branch junction 632 may include a first end opening 636. The first end opening 636 may be positioned longitudinally near the first end 671 of the dividing wall 670 and distal of the proximal fenestration 624 and radially between the sidewall 614 of the main body 610, the sidewall 664 of the auxiliary body 660, and the dividing wall 670. The first end opening 636 may be configured as an inlet opening to enable the body fluid to flow from the retrograde branch segment 642 into the branch junction 632 as further described below. The branch junction 632 may include a second end opening 637. The second end opening 637 may be positioned longitudinally near the first end 671 of the dividing wall 670 and distal of the proximal fenestration 624 and radially between the sidewall 614 of the main body 610, the sidewall 664 of the auxiliary body 660, and the dividing wall 670. The second end opening 637 may be configured as an outlet opening to enable the body fluid to flow from the branch junction 632 into the antegrade branch segment 652 as further described below. The branch junction 632 may include a cannulation opening 640 fluidly coupled to the proximal fenestration 624 of the main body 610. The proximal fenestration 624 and the cannulation opening 640 may be coincident with one another (e.g., configured as a single fenestration through which the main lumen 613 is in fluid communication with the branch junction 632). The proximal fenestration 624 of the main body 610 may be configured as the cannulation opening of the branch junction 632 leading from the main lumen 613 of the main body 110 into the branch junction to enable cannulation of the branch 630 through the proximal fenestration 624 as further described below.

The retrograde branch segment 642 may include a portion of the cavity 628 that is positioned longitudinally between the proximal fenestration 624 and the second end 662 of the auxiliary body. The retrograde branch segment 642 may include a first opening 646 near a first end of the retrograde branch segment as shown in FIG. 13 and a second opening 647 at a second end of the retrograde branch segment as shown in FIG. 10. The first opening 646 may be fluidly coupled to the distal fenestration 626 of the main body 610. The first opening 646 may be configured as an inlet opening to enable the body fluid to flow from the main body 610 into the retrograde branch segment 642. The distal fenestration 626 and the first opening 646 may be coincident with one another (e.g., configured as a single fenestration through which the main lumen 613 is in fluid communication with the retrograde branch segment 642). The second opening 647 may be fluidly coupled to the first end opening 636 of the branch junction 632. The second opening 647 may be configured as an outlet opening to enable the body fluid to flow from the retrograde branch segment 642 into the branch junction 632. The retrograde branch segment 642 may extend from the first opening 646 to the second opening 647 in a retrograde direction as described above with reference to the prosthesis 100.

The antegrade branch segment 652 may include a portion of the cavity 628 that is positioned longitudinally between the proximal fenestration 624 and the second end 662 of the auxiliary body. The antegrade branch segment 652 may be positioned on the opposite side of the dividing wall 670 from the retrograde branch segment 642. In this manner, the retrograde branch segment 642 and the antegrade branch segment 652 may be separated from one another by the dividing wall 670. The antegrade branch segment 652 may include a first opening 656 at a first end of the antegrade branch segment and a second opening 657 at a second end of the antegrade branch segment. The first opening 656 may be fluidly coupled to the second opening 637 of the branch junction 632. The first opening 656 may be configured as an inlet opening to enable the body fluid to flow from the branch junction 632 into the antegrade branch segment 652. The second opening 657 may be configured as an outlet opening to enable the body fluid to flow out of the antegrade branch segment 652. To that end, second opening 657 may be configured as an opening in the sidewall 664 positioned near the second end 662 of the auxiliary body 660. For example, the second opening 657 may be configured as a notch in the second end 662 as shown in FIGS. 10 and 14. A circumferential segment of the sidewall 664 between the dividing walls 670 may be omitted at the second end of the antegrade branch segment 652 as shown in FIG. 14 to form the notch. The notch may extend longitudinally proximally from the second end 662 of the auxiliary body 660 and circumferentially between the dividing walls 670 as shown in FIGS. 10 and 14. The notch may extend proximally to any longitudinal position distal of the proximal fenestration 624. In this manner, the second opening 657 of the antegrade branch segment 652 may be located at any desired longitudinal position between the proximal fenestration 624 and the second end 662 of the auxiliary body 660. For example, the notch may extend to a longitudinal position that is about 15 cm from the proximal end 661 of the main body. In other examples, the notch may extend to a longitudinal position that is any desired distance from the proximal end 661 of the main body. In one example, the second opening 657 may be configured as a fenestration in the sidewall of the auxiliary body. The antegrade branch segment 652 may extend from the first opening 656 to the second opening 657 in an antegrade direction as described above with reference to the prosthesis 100.

In one example, the prosthesis 600 may include two distal fenestrations 626 in the main body 610 and two dividing walls 670 as shown in FIGS. 10-14. The two distal fenestrations 626 may be spaced from one another circumferentially about the sidewall 614 of the main body 610. The two dividing walls 670 may be spaced from one another circumferentially about the sidewall 14 of the main body 610. Each of the two dividing walls 670 may be positioned circumferentially between the two distal fenestrations 626. The two dividing walls 670 may divide the cavity 628 into three chambers. A first chamber may be positioned between the two dividing walls. Two second chambers may be positioned on opposite sides of the first chamber. Each of the two distal fenestrations 626 may be circumferentially aligned with a corresponding one of the second chambers. The proximal fenestration 524 may be circumferentially aligned with the first chamber. Each of the two second chambers may be in fluid communication with the first chamber through an opening in each of the two dividing walls.

The antegrade branch segment 652 may be disposed between the two dividing walls 670 as shown in FIG. 13. The retrograde branch segment 642 may include two retrograde branch segments disposed on opposite sides of the antegrade branch segment 652 and separated from the antegrade branch segment by the dividing walls 670. Each retrograde branch segment 642 may extend circumferentially within the cavity 628. For example, each retrograde branch segment 642 may extend circumferentially between a respective dividing wall 670 and the posterior regions of the main body 610 and the auxiliary body 660 as shown in FIG. 13. The first end opening 636 of the branch junction 632 may include two first end openings. Each first end opening 636 may be fluidly coupled to the second opening 637 of a respective retrograde branch segment 642. In this manner, the body fluid may flow from each retrograde branch segment 642 into the branch junction 632 as further described below.

In other examples, the prosthesis may include any number of dividing walls to define any number of chambers, retrograde branch segments, and/or antegrade branch segments. Additionally, or alternatively, the prosthesis may include any number of proximal fenestrations (e.g., to cannulate any number of antegrade branch segments) and/or any number of distal fenestrations (e.g., to enable fluid to flow from the main body into any number of retrograde branch segments). Preferably, the number of antegrade branch segments may be selected according to the number of branch vessels to which the prosthesis may be coupled. The retrograde branch segments and/or the antegrade branch segments may be spaced from one another circumferentially about the prosthesis.

Figure 15:
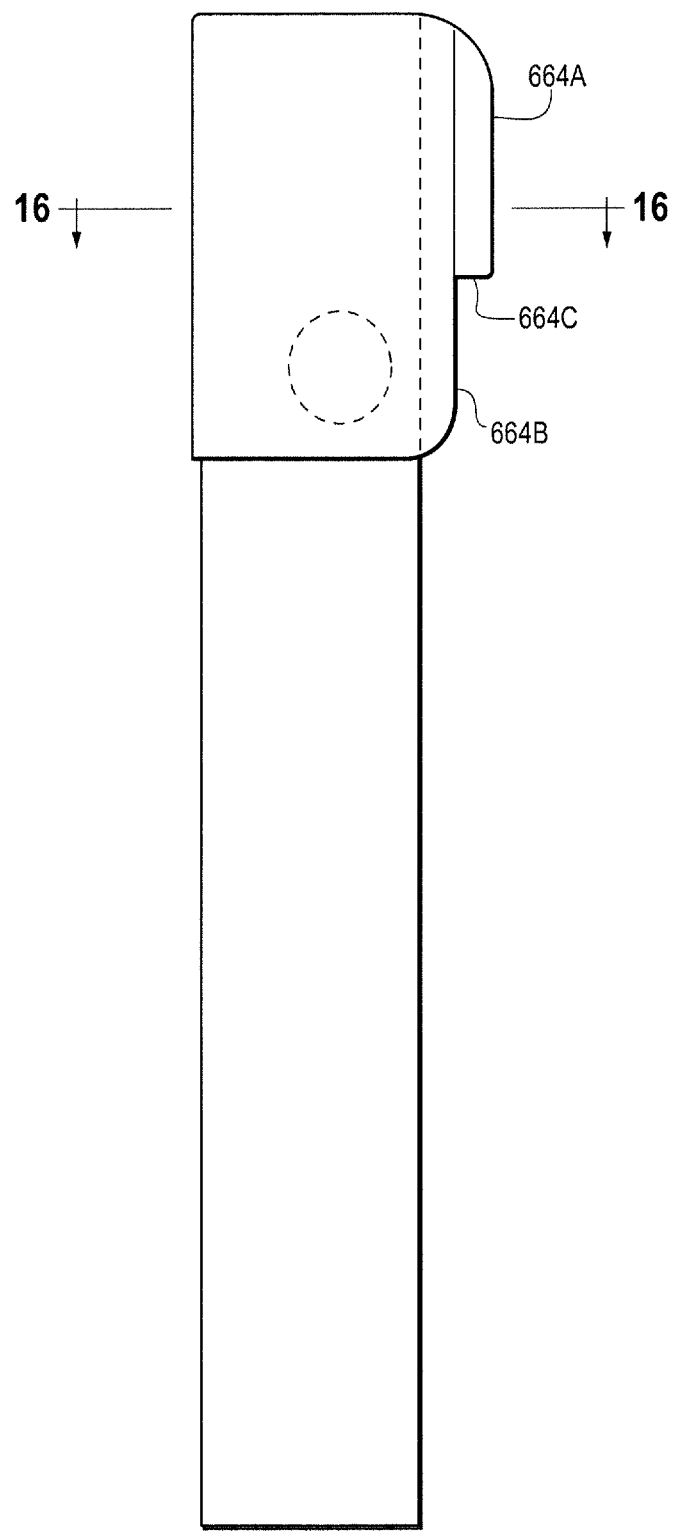
FIG. 15 illustrates one example of an endoluminal prosthesis.

The auxiliary body 660 may or may not have a substantially uniform diameter along the length of the intermediate portion of the sidewall 664. For example, the sidewall 664 may have a substantially uniform diameter along the intermediate portion thereof as shown in FIG. 10. In other words, the intermediate portion of the sidewall 664 may have a substantially cylindrical shape. In one example, the sidewall 664 may have a non-uniform diameter as shown in FIG. 15. The sidewall 664 may include a first portion 664A and a second portion 664B. The first portion 664A may extend longitudinally between the first end 661 of the auxiliary body 660 and a transition 664C. The second portion 664B may extend longitudinally between the transition 664C and the second end 662 of the auxiliary body 660. The first portion 664A may have a larger diameter than the second portion 664B as shown in FIG. 15. The transition 664C may be configured as a step at which the diameter of the sidewall 664 transitions between the larger diameter of the first portion 664A and the smaller diameter of the second portion 664B. The first portion 664A of the auxiliary body 660 may be positioned adjacent to (e.g., at least partially longitudinally aligned with) the proximal portion 618 of the main body 610. The second portion 664B of the auxiliary body 660 may be positioned adjacent to (e.g., at least partially longitudinally aligned with) the distal portion 620 of the main body 610.

Figure 16:
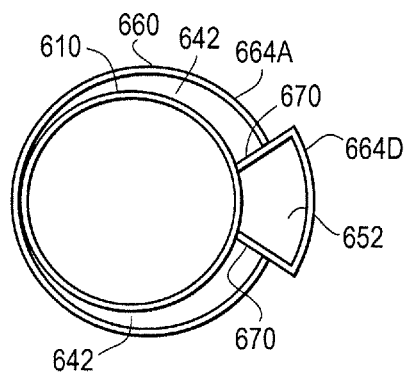
FIG. 16 illustrates a transverse cross sectional view of the endoluminal prosthesis taken along line 16-16 of FIG. 15.

The first portion 664A and/or the second portion 664B of the sidewall 664 of the auxiliary body 660 may have a substantially cylindrical shape. In one example, the first portion 664A may have a non-cylindrical shape as shown in FIG. 16, which is a transverse cross sectional view of the prosthesis 600 taken along line 16-16 of FIG. 15. For example, the first portion 664A may include a protruding portion 664D as shown in FIG. 16. The protruding portion 664D may extend radially outward beyond the remainder of the first portion 664A of the sidewall 664. Along the first portion 664A of the sidewall 664, the dividing walls 670 may extend radially outward beyond the circumferential portion of the sidewall 664 adjacent to the retrograde branch segments 642. In this manner, the portion of the sidewall 664 extending between the dividing walls 670 along the first portion 664A of the sidewall may be positioned radially outward of the remainder of the sidewall 664. Along the first portion 664A, the circumferential portion of the sidewall 664 adjacent to the antegrade branch segment 652 may be positioned radially outward beyond the circumferential portion of the sidewall adjacent to the retrograde branch segments 642 as shown in FIG. 16.

Along the second portion 664B of the sidewall 664 of the auxiliary body 660, the circumferential segment of the sidewall extending between the dividing walls 670 may be omitted as described above with reference to FIGS. 10 and 14. The second opening 657 of the antegrade branch segment 652 may be positioned longitudinally at the transition 664C between the first portion 664A and the second portion 664B of the auxiliary body 660. In this manner, the second opening 657 of the antegrade branch segment 652 may be positioned at any longitudinal position between the proximal fenestration 624 and the second end 662 of the auxiliary body 660. Omitting the circumferential segment of the sidewall 664 extending between the dividing walls 670 distal of the second opening 657 of the antegrade branch segment 652 may avoid the formation of a pocket distal of the second opening 657. Such a pocket may interfere with cannulation of the antegrade branch segment (e.g., by catching a delivery device navigated through the antegrade branch segment) and/or collect excess body fluid which may result in clot formation (e.g., thrombosis).

Figure 17:
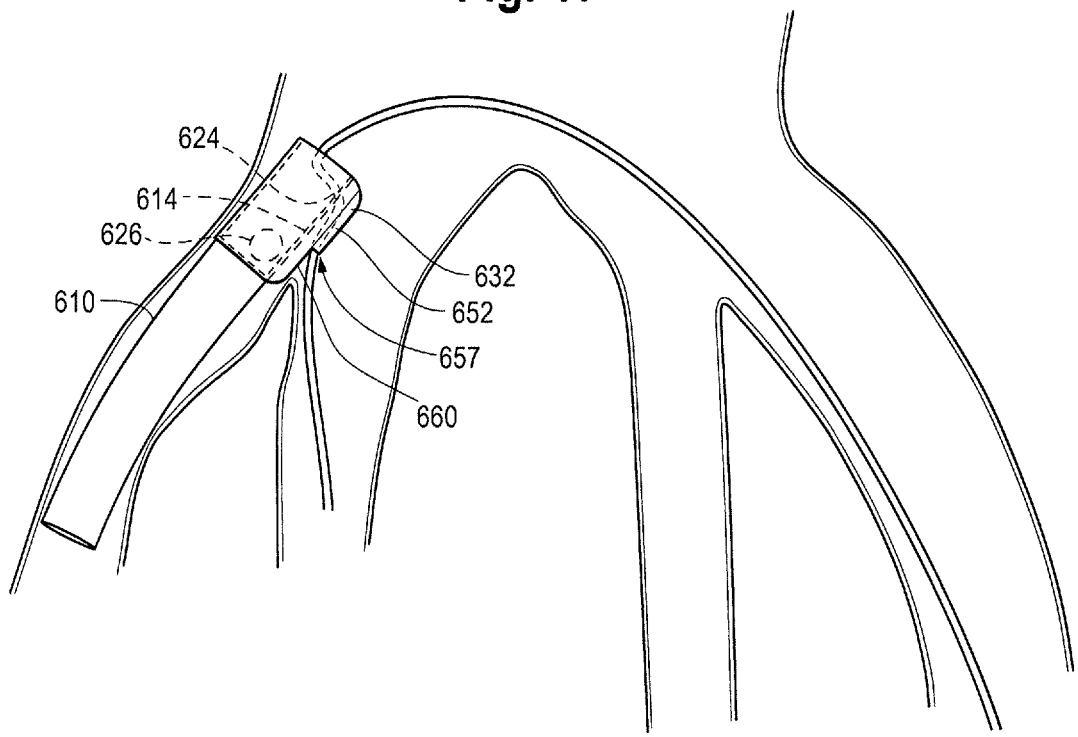
FIGS. 17-18 illustrate deployment of the endoluminal prosthesis shown in FIG. 10 within a body vessel and deployment of exemplary extension prostheses within the endoluminal prosthesis.
Figure 18:
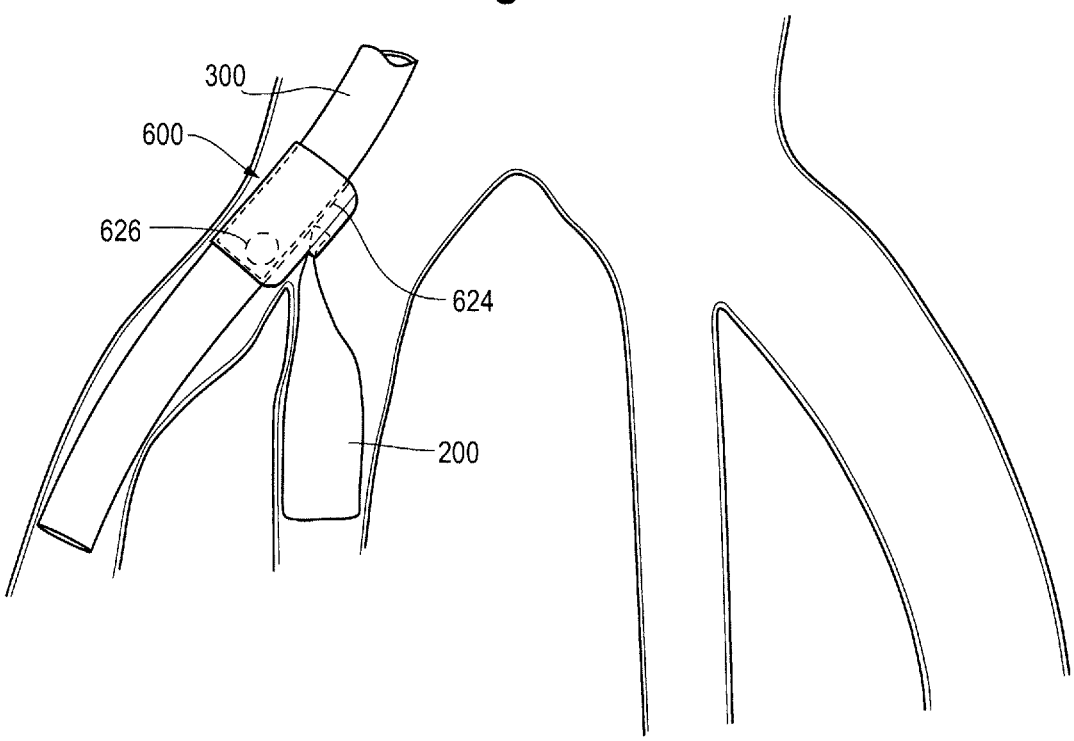

The prosthesis 600 may be deployed generally as described above with reference to FIGS. 3-6. For example, to cannulate the branch 630, an introducer (e.g., the second introducer) may be advanced into the branch junction 632 via the proximal fenestration 624 and then further advanced out of the branch 630 via the antegrade branch segment 652 as shown in FIG. 17. For clarity, the dividing walls 670 are not shown in FIG. 17. Upon passing the introducer through the proximal fenestration 624, the introducer may be disposed within the branch junction 632 and between the dividing walls 670. Upon further advancement of the introducer, the introducer may be guided between the dividing walls 670 toward the second opening 657 of the antegrade branch segment 552. The branch extension prosthesis 200 may be deployed within the antegrade branch segment 652 as shown in FIG. 18 using the second introducer. The main extension prosthesis 300 may be deployed within the prosthesis 600. Upon deployment of the main extension prosthesis 300, the proximal fenestration 624 may be sealed by the overlap between the main extension prosthesis and the main body 610 of the prosthesis 600.

With the main extension prosthesis 300 (or another suitable extension prosthesis) deployed within the main body 610 as described above, the body fluid may enter the main body 610 of the prosthesis 600 at the proximal end 611 and flow distally to the distal fenestrations 626. The body fluid may flow through the distal fenestrations 626 and the first openings 646 of the retrograde branch segments 642 to enter the retrograde branch segments at the longitudinal position shown in FIG. 14. The body fluid may flow radially outward from the main body 610 into each retrograde branch segment 642. The body fluid may be substantially prevented from exiting the branch at the longitudinal position shown in FIG. 14 by the dividing walls 670 separating the retrograde branch segment 642 from the antegrade branch segment 652. The body fluid may flow in the retrograde direction through the retrograde branch segments 642.

The body fluid may flow through the second openings 647 of the retrograde branch segments 642 and the first end openings 636 of the branch junction 632 to enter the branch junction 632 at the longitudinal position shown in FIG. 13. The body fluid may overflow the dividing walls 670 within the branch junction 632 at the longitudinal position shown in FIG. 11. In other words, the body fluid may flow in the retrograde direction to the first ends 671 of the dividing walls 670 and change direction to flow in the antegrade direction toward the antegrade branch segment 652. The retrograde branch segment 642 and the antegrade branch segment 652 may be separated from one another by the dividing wall 670 and in fluid communication with one another through the branch junction 632 as described above. The body fluid may flow through the second end opening 637 of the branch junction 632 and the first opening 656 of the antegrade branch segment 652 to enter the antegrade branch segment at the longitudinal position shown in FIG. 13. The body fluid may flow in the antegrade direction through the antegrade branch segment 652. The body fluid may flow through the second opening 657 of the antegrade branch segment at the longitudinal position shown in FIG. 14 to exit the prosthesis 600.

The position of the supply point (e.g., the first opening 646) of the branch 630 distal of the overlap region between the main extension prosthesis 300 and the main body 610 may enable the prosthesis 600 to have a reduced neck length as described above with reference to FIGS. 1-2. In this manner, the prosthesis 600 may be configured for placement within a patient having a relatively short common iliac artery as described above with reference to the prosthesis 100.

In any of the examples described herein, the prosthesis may have any suitable size. Preferably, the prosthesis may be sized and shaped based on the desired location within the body in which the prosthesis is to be implanted. For example, the prosthesis may be configured for implantation within a 16 mm common iliac artery. To that end, the main body 110 of the prosthesis 100 and/or the main body 510 of the prosthesis 500 may have a diameter of about 12 mm. Additionally, or alternatively, the branch 130 (or a portion thereof) of the prosthesis 100 and/or the branch 530 (or a portion thereof) of the prosthesis 500 may have a diameter of between about 6 mm and about 8 mm. The auxiliary body 660 of the prosthesis 600 may have a diameter of about 16 mm. Additionally, or alternatively, the main body 610 may have a diameter of about 12 mm. The relative diameters of the main body 610 and the auxiliary body 660 may be tailored to provide a desired cross sectional flow area through the retrograde branch segments and a desired outer diameter of the prosthesis. In any of the embodiments described herein, the main body of the prosthesis may have a length of about 86 cm. The proximal fenestration may be spaced from the proximal end of the main body by about 5 mm. Additionally, or alternatively, the distal fenestration may be spaced from the proximal end of the main body by about 20 mm.

In any of the examples described herein, radiopaque markers may be placed at any desired positions along the prosthesis. For example, radiopaque markers may be placed at the proximal fenestration and/or the distal fenestration to aid in placing the supply port and/or the cannulation port at a desired position within the body vessel.

While various embodiments of the invention have been described, the invention is not to be restricted except in light of the attached claims and their equivalents. Drawings in the figures illustrating various embodiments are not necessarily to scale. Some drawings may have certain details magnified for emphasis, and any different numbers or proportions of parts should not be read as limiting unless so-designated in the present disclosure. Those skilled in the art will appreciate that embodiments not expressly illustrated herein may be practiced within the scope of the present invention, including those features described herein for different embodiments, which may be combined with each other and/or with currently-known or future-developed technologies while remaining within the scope of the claims presented herein. Moreover, the advantages described herein are not necessarily the only advantages of the invention and it is not necessarily expected that every embodiment of the invention will achieve all of the advantages described.

We claim:

1. An endoluminal prosthesis comprising:
a tubular main body comprising a proximal end opening, a distal end opening, a main lumen extending between the proximal end opening and the distal end opening, a sidewall, a first fenestration in the sidewall, and a second fenestration in the sidewall positioned distal of the first fenestration; and
a tubular auxiliary body disposed about the main body and comprising a sidewall, an outlet opening in the sidewall, a first end attached to the main body proximal of the first fenestration, a second end attached to the main body distal of the second fenestration, and a first dividing wall attached to the sidewall of the main body and the sidewall of the auxiliary body and extending longitudinally at least partially between the first end of the auxiliary body and the second end of the auxiliary body;
wherein a cavity is disposed between the sidewall of the main body and the sidewall of the auxiliary body and comprises a first chamber and a second chamber disposed on opposite sides of the first dividing wall and in fluid communication with one another through an opening in the first dividing wall, the main lumen is in fluid communication with the first chamber through the first fenestration, the main lumen is in fluid communication with the second chamber through the second fenestration, and the first chamber is in fluid communication with a point external of the prosthesis through the outlet opening of the auxiliary body.

2. The prosthesis of claim 1, wherein the first dividing wall comprises a first end that is spaced longitudinally from the first end of the auxiliary body and a second end that is attached to the second end of the auxiliary body, and the opening in the first dividing wall comprises a gap between the first end of the auxiliary body and the first end of the first dividing wall.

3. The prosthesis of claim 1, wherein the main body comprises a first portion positioned within the auxiliary body and a second portion positioned outside of the auxiliary body and extending distally from the auxiliary body.

4. The prosthesis of claim 3, wherein the auxiliary body comprises a support structure attached to the sidewall of the auxiliary body, and the second portion of the main body is free of a support structure.

5. The prosthesis of claim 1, further including a second dividing wall spaced circumferentially from the first dividing wall about the main body, a third fenestration spaced from the second fenestration about the main body, a third chamber spaced from the second chamber circumferentially about the main body, wherein the second and third chambers are positioned on opposite sides of the first chamber, wherein the main lumen is in fluid communication with the second and third chambers through one of the second and third fenestrations, and wherein the second and third chambers are in fluid communication with the first chamber through an opening in each of the dividing walls.

6. The prosthesis of claim 5, wherein each of the first and second dividing walls extends longitudinally within the cavity and has a first end and a second end, wherein the first ends are longitudinally spaced from the first end of the auxiliary body to form a passage between the two chambers, and the second ends are attached to the second end of the auxiliary body.

7. The prosthesis of claim 5, wherein each of the first and second dividing walls has a fenestration such that each of the first and second chambers are in fluid communication with each other.

8. The prosthesis of claim 1, wherein the second chamber is configured to provide retrograde fluid flow through the second chamber to the first chamber and the first chamber is and the first chamber is configured to provide antegrade fluid flow through the first chamber and out of the outlet opening.

9. The prosthesis of claim 1, wherein a posterior region of the sidewall of the main body is attached to a posterior region of the sidewall of the auxiliary body.

10. The prosthesis of claim 1, wherein the first end and the second end of the auxiliary body are sealingly attached to the sidewall of the main body to create a closed cavity except for the outlet opening.

11. An endoluminal prosthesis comprising:
a tubular main body comprising a proximal end, a proximal end opening, a distal end, a distal end opening, a main lumen extending between the proximal end opening and the distal end opening, a sidewall, a first fenestration in the sidewall of the main body, and second and third fenestrations in the sidewall of the main body positioned distal of the first fenestration; and a tubular auxiliary body disposed about a proximal portion of the main body and comprising a sidewall, an outlet opening, a first end attached to the main body proximal of the first fenestration, a second end attached to the main body distal of the second and third fenestrations to create a substantially closed cavity between the main body and the tubular auxiliary body, a first dividing wall in the substantially closed cavity attached to the sidewall of the main body and to the sidewall of the auxiliary body and extending longitudinally at least partially between the first end of the auxiliary body and the second end of the auxiliary body;

a second dividing wall in the substantially closed cavity spaced circumferentially from the first dividing wall and attached to the sidewall of the main body and the sidewall of the auxiliary body and extending longitudinally at least partially between the first end of the auxiliary body and the second end of the auxiliary body;

a first chamber between the first and second dividing walls and second and third chambers disposed on opposite sides of the first and second dividing walls and in fluid communication with one another and the first chamber through openings in the dividing walls;

wherein the main lumen is in fluid communication with the first chamber through the first fenestration, the main lumen is in fluid communication with the second chamber through the second fenestration, the main lumen is in fluid communication with the third chamber through the third fenestration, and the first chamber is in fluid communication with a point external of the prosthesis through the outlet opening.

12. The prosthesis of claim 11, wherein the openings in the first and second dividing walls are gaps between first ends of the dividing walls and the first end of the auxiliary body.

13. The prosthesis of claim 11, wherein the openings in the first and second dividing walls are fenestrations in the first and second dividing walls.

14. The prosthesis of claim 11, wherein a distal portion of the main body extends distally from the second end of the auxiliary body.

15. The prosthesis of claim 11, wherein the first ends of the first and second dividing walls extend longitudinally between the first end of the auxiliary body and the first fenestration.

16. The prosthesis of claim 11, wherein the main body is offset from the auxiliary body such that a posterior portion of the sidewall of the main body is attached to a posterior portion of the side wall of the auxiliary body.

17. The prosthesis of claim 11, wherein each of the second and third chambers is configured to provide retrograde fluid flow through the second and third chambers to the first chamber, and the first chamber is configured to provide antegrade fluid flow through the first chamber and out of the outlet opening.

18. An endoluminal prosthesis comprising:

a tubular main body comprising a proximal end, a proximal end opening, a distal end, a distal end opening, a main lumen extending between the proximal end opening and the distal end opening, a sidewall, a first fenestration in the sidewall of the main body, and second and third fenestrations in the sidewall of the main body positioned distal of the first fenestration; and a tubular auxiliary body disposed about a proximal portion of the main body and comprising a sidewall, an outlet opening, a first end attached to the main body proximal of the first fenestration, a second end attached to the main body distal of the second and third fenestrations to create a substantially closed cavity between the main body and the tubular auxiliary body, a first dividing wall in the substantially closed cavity attached to the sidewall of the main body and to the sidewall of the auxiliary body and extending longitudinally at least partially between the first end of the auxiliary body and the second end of the auxiliary body;

a second dividing wall in the substantially closed cavity spaced circumferentially from the first dividing wall and attached to the sidewall of the main body and the sidewall of the auxiliary body and extending longitudinally at least partially between the first end of the auxiliary body and the second end of the auxiliary body;

a first chamber between the first and second dividing walls and second and third chambers disposed on opposite sides of the first and second dividing walls and in fluid communication with one another and the first chamber through openings in the dividing walls;

wherein the main lumen is in fluid communication with the first chamber through the first fenestration, wherein the second fenestration is disposed in the second chamber and the main lumen is in fluid communication with the second chamber through the second fenestration, wherein the third fenestration is disposed within the third chamber and the main lumen is in fluid communication with the third chamber through the third fenestration, and wherein the first chamber is in fluid communication with a point external of the prosthesis through the outlet opening.

19. The prosthesis of claim 18, wherein the openings in the first and second dividing walls are gaps between the first ends of the dividing walls and the first end of the auxiliary body.

20. The prosthesis of claim 18, wherein the openings in the first and second dividing walls are fenestrations in the first and second dividing walls.

* * * * *